(12) United States Patent  
East

(10) Patent No.: US 7,192,953 B2
(45) Date of Patent: Mar. 20, 2007

(54) ANTIBACTERIAL AGENTS

(75) Inventor: Stephen Peter East, Abingdon (GB)

(73) Assignee: Vernalis (Oxford) Limited (GB)

( * ) Notice: Subject to any disclaimer, the term of this patent is extended or adjusted under 35 U.S.C. 154(b) by 0 days.

(21) Appl. No.: 10/537,346

(22) PCT Filed: Dec. 1, 2003

(86) PCT No.: PCT/GB03/05179

§ 371 (c)(1), (2), (4) Date: Jan. 23, 2006

(87) PCT Pub. No.: WO2004/050638

PCT Pub. Date: Jun. 17, 2004

(65) Prior Publication Data

US 2006/0128811 A1    Jun. 15, 2006

(30) Foreign Application Priority Data

Dec. 5, 2002   (GB)   ............... 0228365.3

(51) Int. Cl.
*A61K 31/55* (2006.01)
*A61K 31/50* (2006.01)
*A61K 31/415* (2006.01)
*C07D 285/36* (2006.01)
*C07D 237/02* (2006.01)
*C07D 231/00* (2006.01)

(52) U.S. Cl. ............... 514/218; 514/247; 514/403; 540/545; 540/554; 540/604; 540/605; 544/224; 548/356.1

(58) Field of Classification Search ............... None
See application file for complete search history.

(56) References Cited

FOREIGN PATENT DOCUMENTS

| WO | WO 95 29892 A | 11/1995 |
|---|---|---|
| WO | WO 95 33731 A | 12/1995 |

OTHER PUBLICATIONS

K. Tamaki et al.: "Synthesis and Structure-Activity Relationships of Gelatinase Inhibitors" Chemical and Pharmaceutical Bulletin., vol. 43, No. 11, 1995, pp. 1883-1893, XP002165817 Pharmaceutical Societe of Japan. Tokyo., JP, ISSN: 0009-2363 p. 1883; example 29-31.

*Primary Examiner*—Paul A Zucker
(74) *Attorney, Agent, or Firm*—Banner & Witcoff, Ltd.

(57) ABSTRACT

Compounds of formula (I) have antibacterial activity; wherein Q represents a radical of formula —N(OH)CH(=O) or formula —C(=O)NH(OH); Y represents —C(=O)—, —C(=S)—, —S(=O)—, or —SO$_2$—; $R_1$ represents hydrogen, $C_1$–$C_6$ alkyl or $C_1$–$C_6$ alkyl substituted by one or more halogen atoms, or, except when Q is a radical of formula —N(OH)CH(=O), a hydroxy, $C_1$–$C_6$ alkoxy, $C_1$–$C_6$ alkenyloxy, halogen, amino, $C_1$–$C_6$ alkylamino, or di-($C_1$–$C_6$ alkyl)amino group; $R_2$ represents a substituted or unsubstituted $C_1$–$C_6$ alkyl, $C_1$–$C_3$ alkyl-O—$C_1$–$C_3$ alkyl, $C_1$–$C_3$ alkyl-S—$C_1$–$C_3$ alkyl, cycloalkyl($C_1$–$C_3$ alkyl)-, aryl ($C_1$–$C_3$alkyl)-, heterocyclyl($C_1$–$C_3$ alkyl)-, or $R^1R^2N$—$C_1$–$C_3$ alkyl group wherein $R^1$ represents hydrogen or $C_1$–$C_3$ alkyl and $R^2$ represents $C_1$–$C_3$ alkyl, or $R^1R^2N$- represents a cyclic amino group; $R_3$ and $R_4$ taken together with the nitrogen atoms to which they are respectively attached form a saturated heterocyclic ring of from 4 to 7 ring atoms, which may be fused to a second carbocyclic or heterocyclic ring, either of which rings may optionally be substituted; and A represents a primary, secondary or tertiary amino group or a group —$R_5$, —$OR_5$, wherein $R_5$ is a substituted or unsubstituted $C_1$–$C_6$ alkyl, $C_2$–$C_6$ alkenyl, $C_2$–$C_6$ alkynyl, cycloalkyl, aryl, heterocyclyl, $C_1$–$C_3$ alkyl-O—$C_1$–$C_3$alkyl, $C_1$–$C_3$ alkyl-S—$C_1$–$C_3$ alkyl, cycloalkyl ($C_1$–$C_3$ alkyl)-, heterocyclic($C_1$–$C_3$ alkyl, aryl($C_1$–$C_3$ alkyl)-or $R^1R^2N$—$C_1$–$C_3$ alkyl group wherein $R^1$ represents hydrogen or $C_1$–$C_3$ alkyl and $R^2$ represents $C_1$–$C_3$ alkyl, or $R^1R^2N$-represents a cyclic amino group

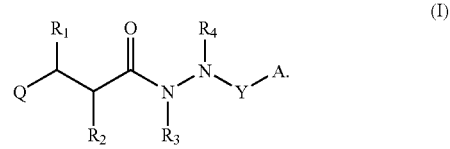

(I)

21 Claims, No Drawings

ANTIBACTERIAL AGENTS

This application is a U.S. National Stage application of co-pending PCT application PCT/GB2003/005179, filed Dec. 1, 2003, which claims the priority of Great Britain Patent Application No. 0228365.3, filed Dec. 5, 2002. These applications are incorporated herein by reference in their entireties.

This invention relates to novel hydroxamic acid and N-formyl hydroxylamine derivatives having antibacterial activity, to methods of treatment using such compounds, and to pharmaceutical and veterinary compositions comprising such compounds.

BACKGROUND TO THE INVENTION

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes, and/or which are effective against the causative organisms of community acquired respiratory infections, and/or which are selective in their pharmacological activity, thus reducing risk of unwanted side effects.

Amongst the Gram-positive pathogens, such as staphylococci, streptococci, mycobacteria and enterococci, resistant strains have evolved/arisen which makes them particularly difficult to eradicate. Examples of such strains are methicillin resistant *Staphylococcus aureus* (MRSA), methicillin resistant coagulase negative *Staphylococci* (MRCNS), penicillin resistant *Streptococcus pneumoniae* and multiply resistant *Enterococcus faecium*

BRIEF DESCRIPTION OF THE INVENTION

This invention makes available a new class of hydroxamic acid and N-formyl hydroxylamine derivatives having antibacterial activity. The compounds are characterised inter alia by the presence of a cyclic diazole feature in their structural backbone.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

RELATED PRIOR ART

Although there are many publications disclosing both hydroxamic acid and N-formyl hydroxylamine derivatives as inhibitors of various metalloenzymes such as angiotensin converting enzyme, enkephalinase and the matrix metalloproteinases, there are relatively few relating to such compounds as antibacterial agents. The following patent publications are relevant in that connection:

| | |
|---|---|
| WO 99/39704 | (British Biotech) |
| WO 99/57097 | (Versicor) |
| WO 99/59568 | (British Biotech) |
| WO 00/35440 | (British Biotech) |
| WO 00/44373 | (British Biotech) |
| WO 00/58294 | (British Biotech) |
| WO 00/61134 | (British Biotech) |
| WO 01/10835 | (British Biotech) |
| WO 01/38561 | (Questcor) |
| WO 01/40198 | (Aventis) |
| WO 01/42431 | (Bayer) |
| WO 01/44178 | (Versicor) |
| WO 01/44179 | (Versicor) |
| WO 01/85160 | (SmithKline Beecham) |
| WO 01/85170 | (SmithKline Beecham) |
| WO 02/28829 | (Questcor) |
| WO 02/41886 | (British Biotech) |
| WO 02/50081 | (British Biotech) |

WO 02/070541 SmithKline Beecham) relates to PDF inhibitor compounds which have a hydrazide feature in the backbone and an N-formylhydroxylamino metal binding group.

In addition the natural antibiotic actinonin (see for example J.C.S Perkin I, 1975, 819) is a hydroxamic acid derivative of Structure (A):

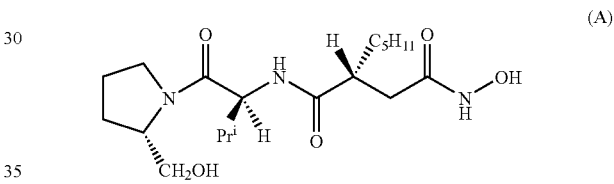

which is now known to act by inhibition of PDF. In addition to actinonin, various structural analogues of actinonin have also been shown to have antibacterial activity (see for example Broughton et al. (Devlin et al. Journal of the Chemical Society. Perkin Transactions 1 (9):830–841, 1975; Broughton et al. Journal of the Chemical Society. Perkin Transactions 1 (9):857–860, 1975).

The matlystatin group of compounds share a number of structural similarities with actinonin. Both are peptidic molecules with functional hydroxamic acid metal binding groups (Ogita et al., J. Antibiotics. 45(11):1723–1732; Tanzawa et al., J. Antibiotics. 45(11):1733–1737; Haruyama et al., J. Antibiotics. 47(12):1473–1480; Tamaki et al., J. Antibiotics. 47(12):1481–1492). The matlystatins and their close structural analogues are characterised by the presence in the molecule of a divalent piperazin-1,6-diyl group, i.e.

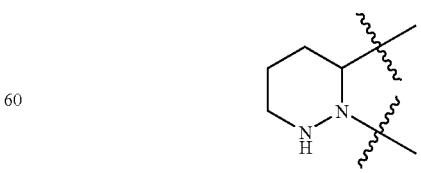

In view of their close structural similarity to actinonin, the observation that actinonin inhibits PDF implies that matlystatin compounds may also inhibit PDF.

For a recent review of peptide deformylase inhibitors, see Clements et. al., Curr. Med. Chem.—Anti-infective Agents, 2002, 1, 239–249.

The following patent publications disclose N-formyl hydroxylamine structures:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (GlaxoWellcome) |
| WO 98/47863 | (Labs Jaques Logeais) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis.

In addition to these, U.S. Pat. No. 4,738,803 (Roques et al.) also discloses N-formyl hydroxylamine derivatives. However, these compounds are disclosed as enkephalinase inhibitors and are proposed for use as antidepressants and hypotensive agents. Also, WO 97/38705 (Bristol-Myers Squibb) discloses certain N-formyl hydroxylamine derivatives as enkephalinase and angiotensin converting enzyme inhibitors.

There are too many publications relating to metalloenzyme inhibiting hydroxylamic acid derivatives to summarise effectively. However a recent review, Whittaker et. al. Chem. Rev. 1999, 99, 2735, provides an overview of that art.

DESCRIPTION OF THE INVENTION

The present invention provides a compound of formula (I) or a pharmaceutically or veterinarily acceptable salt, hydrate or solvate thereof

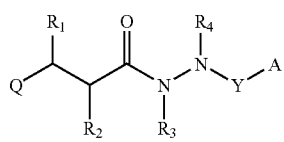

(I)

wherein

Q represents a radical of formula —N(OH)CH(=O) or formula
—C(=O)NH(OH);

Y represents —C(=O)—, —C(=S)—, —S(=O)—, or —SO$_2$—;

R$_1$ represents hydrogen, C$_1$–C$_6$ alkyl or C$_1$–C$_6$ alkyl substituted by one or more halogen atoms, or, except when Q is a radical of formula —N(OH)CH(=O), a hydroxy, C$_1$–C$_6$ alkoxy, C$_1$–C$_6$ alkenyloxy, halogen, amino, C$_1$–C$_6$ alkylamino, or di-(C$_1$–C$_6$ alkyl)amino group;

R$_2$ represents a substituted or unsubstituted C$_1$–C$_6$ alkyl, C$_1$–C$_3$ alkyl-O-C$_1$–C$_3$ alkyl, C$_1$–C$_3$ alkyl-S—C$_1$–C$_3$ alkyl, cycloalkyl(C$_1$–C$_3$ alkyl)-, aryl(C$_1$–C$_3$ alkyl)-, heterocyclyl (C$_1$–C$_3$ alkyl)-, or R$^1$R$^2$N—C$_1$–C$_3$ alkyl group wherein R$^1$ represents hydrogen or C$_1$–C$_3$ alkyl and R$^2$ represents C$_1$–C$_3$ alkyl, or R$^1$R$^2$N— represents a cyclic amino group;

R$_3$ and R$_4$ taken together with the nitrogen atoms to which they are respectively attached form a saturated heterocyclic ring of from 4 to 7 ring atoms, which may be fused to a second carbocyclic or heterocyclic ring, either of which rings may optionally be substituted; and A represents a primary, secondary or tertiary amino group or a group —R$_5$, —OR$_5$, wherein R$_5$ is a substituted or unsubstituted C$_1$–C$_6$ alkyl, C$_2$–C$_6$ alkenyl, C$_2$–C$_6$ alkynyl, cycloalkyl, aryl, heterocyclyl, C$_1$–C$_3$ alkyl-O—C$_1$–C$_3$ alkyl, C$_1$–C$_3$ alkyl-S—C$_1$–C$_3$ alkyl, cycloalkyl(C$_1$–C$_3$ alkyl)-, heterocyclic(C$_1$–C$_3$ alkyl, aryl(C$_1$–C$_3$ alkyl)-, or R$^1$R$^2$N— C$_1$–C$_3$ alkyl group wherein R$^1$ represents hydrogen or C$_1$–C$_3$ alkyl and R$^2$ represents C$_1$–C$_3$ alkyl, or R$^1$R$^2$N— represents a cyclic amino group.

In another aspect, the invention provides a method for the treatment of bacterial infections in humans and non-human mammals, which comprises administering to a subject suffering such infection an antibacterially effective dose of a compound of formula (I) as defined above. Also included in the invention is the use of a compound of formula (I) as defined above for inhibiting bacterial growth in vitro and in vivo in mammals, and the use of such a compound for the manufacture of a composition for treating bacterial infection by inhibiting bacterial growth.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

As used herein terms of the form "(C$_a$–C$_b$)alkyl" where a and b are integers refer to a straight or branched chain alkyl moiety having from a to b carbon atoms. Thus, for example, the term "(C$_1$–C$_6$)alkyl" means a straight or branched chain alkyl moiety having from 1 to 6 carbon atoms, and includes, for example, methyl, ethyl, n-propyl, isopropyl, n-butyl, isobutyl, sec-butyl, t-butyl, n-pentyl and n-hexyl.

As used herein terms of the form "divalent (C$_a$–C$_b$) alkylene radical" where a and b are integers refer to a saturated hydrocarbon chain having from a to b carbon atoms and two unsatisfied valencies.

As used herein terms of the form "(C$_a$–C$_b$)alkenyl" where a and b are integers refer to straight or branched chain alkenyl moiety having from a to b carbon atoms having at least one double bond of either E or Z stereochemistry where applicable. Thus, for example, the term "(C$_1$–C$_6$)alkenyl" means a straight or chain alkenyl moiety having from 2 to 6 carbon atoms having at least one double bond, and includes, for example, vinyl, allyl, 1- and 2-butenyl and 2-methyl-2-propenyl.

As used herein the term "C$_a$–C$_b$ alkynyl" where a and b are integers refers to straight chain or branched chain hydrocarbon groups having from two to six carbon atoms and having in addition one triple bond. Thus, for example, the term "(C$_1$–C$_6$)alkynyl" would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl.

As used herein the unqualified term "heterocyclyl" or "heterocyclic" includes "heteroaryl" as defined above, and in particular means a 5–7 membered aromatic or non-aromatic heterocyclic ring containing one or more heteroatoms selected from S, N and O, including for example, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, maleimido and succinimido groups.

Unless otherwise specified in the context in which it occurs, the term "substituted" as applied to any moiety herein means substituted with up to four substituents, each of which independently may be, for example, $(C_1$–$C_6)$alkyl, $(C_1$–$C_6)$alkoxy, hydroxy, hydroxy$(C_1$–$C_6)$alkyl, mercapto, mercapto$(C_1$–$C_6)$alkyl, $(C_1$–$C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1$–$C_6)$alkyl group.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the R$_2$ group is R.

In the compounds of the invention, in relation to the groups Q, R$_1$, R$_2$, R$_3$, R$_4$, Y and A, separately and in combination:

The Group Q

It is currently preferred that Q is an N-formyl hydroxylamine group —N(OH)CH(=O).

The Radical —Y—

It is currently preferred that —Y— is —C(=O) or —SO$_2$—.

The Group R$_1$

R$_1$ may be, for example, hydrogen, methyl, trifluoromethyl or, in the case where Q is a hydroxamic acid group HONHCO—, fluorine. Hydrogen is currently preferred.

The Group R$_2$

R$_2$ may be, for example:

optionally substituted $C_1$–$C_6$ alkyl, $C_3$–$C_6$ alkenyl, $C_3$–$C_6$ alkynyl or cycloalkyl;

phenyl($C_1$–$C_6$ alkyl)-, phenyl($C_3$–$C_6$ alkenyl)- or phenyl($C_3$–$C_6$ alkynyl)-optionally substituted in the phenyl ring;

cycloalkyl($C_1$–$C_6$ alkyl)-, cycloalkyl($C_3$–$C_6$ alkenyl)- or cycloalkyl($C_3$–$C_6$ alkynyl)-optionally substituted in the cycloalkyl ring; or $CH_3(CH_2)_pO(CH_2)_q$- or $CH_3(CH_2)_pS(CH_2)_q$-, wherein p is 0, 1, 2 or 3 and q is 1, 2 or 3.

Specific examples of R$_2$ groups include methyl, ethyl, n- and iso-propyl, n- and iso-butyl, n-pentyl, iso-pentyl, 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-Chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, pyrid-2-ylmethyl, pyrid-3-ylmethyl, pyrid-4-ylmethyl, phenylpropyl, 4-Chlorophenylpropyl, 4-methylphenylpropyl, 4-methoxyphenylpropyl, benzyl, 4-Chlorobenzyl, 4-methylbenzyl, and 4-methoxybenzyl.

Presently preferred groups at R$_2$ are $(C_1$–$C_6)$alkyl-, cycloalkylmethyl-, $(C_1$–$C_3)$alkyl-S—$(C_1$–$C_3)$alkyl-, or $(C_1$–$C_3)$alkyl-O—$(C_1$–$C_3)$alkyl-, especially n-propyl, n-butyl, n-pentyl, cyclopentylmethyl, cyclopentylethyl, cyclohexylmethyl or cyclohexylethyl.

The Ring Formed by R$_3$ and R$_4$ and the Nitrogens to which they are Attached

Examples of such rings are the following, wherein R represents hydrogen or $C_1$–$C_4$ alkyl

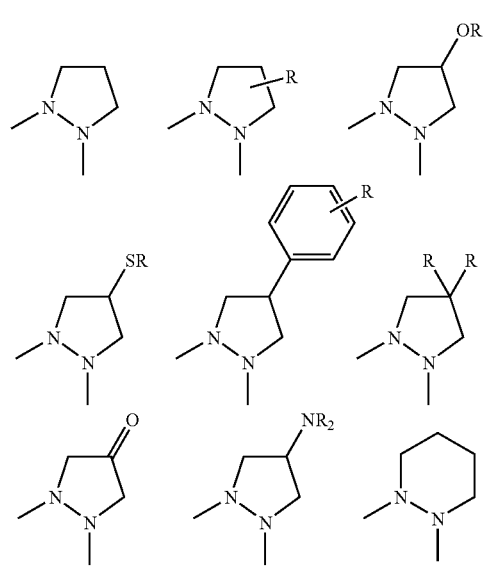

In the above rings, where a sulfur atom is present as a ring member, the equivalent structures wherein that sulfur is oxidised to —SO— or —SO$_2$— are also examples of ring structures which may be formed by R$_3$ and R$_4$ and the nitrogens to which they are attached.

The Group A

The group A is a primary, secondary or tertiary amino group or a group —R$_5$, or —OR$_5$. When A is —R$_5$, or —OR$_5$, the R$_5$ group may be, for example, any of those given as R$_2$ examples above, or a group of formula (II) as defined below, including such specific examples of groups (II) as morpholinyl, furanyl, thienyl, phenyl, and benzyl.

Presently it is preferred that A is a secondary or tertiary amino group, and in the latter case it may be a non-cyclic or a cyclic amino group. For example, A may be an amino group of formula —NR$_6$R$_7$ wherein R$_6$ and R$_7$ independently represent a radical of formula (II)

$$\text{—(Alk}^1\text{)}_m\text{—(X)}_p\text{—(Alk}^2\text{)}_n\text{—Z} \quad \text{(II)}$$

wherein m, p and n are independently 0 or 1;

Z represents hydrogen or a carbocyclic or heterocyclic ring of 5 to 7 ring atoms which is optionally fused to a saturated or unsaturated carbocyclic or heterocyclic second ring of 5 to 7 ring atoms;

Alk$^1$ and Alk$^2$ independently represent divalent C$_1$–C$_3$ alkylene radicals;

X represents —O—, —S—, —S(O)—, —S(O$_2$)—, —C(=O)—, —NH—, —NR$_7$— where R$_7$ is C$_1$–C$_3$ alkyl;

and wherein

Alk$^1$, Alk$^2$ and Z when other than hydrogen, independently are optionally substituted by (C$_1$–C$_3$)alkyl, (C$_2$–C$_3$)alkenyl, or (C$_2$–C$_3$)alkynyl, phenyl, optionally substituted by (C$_1$–C$_3$)alkyl, (C$_1$–C$_3$) alkoxy, halo, nitro, amino, mono- or di-(C$_1$–C$_3$)alkylamino, cyano or trifluoromethyl;

monocyclic 5 or 6-membered heterocyclic, optionally substituted by (C$_1$–C$_3$)alkyl, (C$_1$–C$_3$)alkoxy, halo, nitro, amino, mono- or di-(C$_1$–C$_3$)alkylamino, cyano or trifluoromethyl benzyl, optionally substituted in the phenyl ring by (C$_1$–C$_3$)alkyl, (C$_1$–C$_3$)alkoxy, halo, nitro, amino, mono- or di-(C$_1$–C$_3$)alkylamino, cyano or trifluoromethyl, hydroxy, phenoxy, (C$_1$–C$_6$)alkoxy, or hydroxy(C$_1$–C$_6$) alkyl, mercapto, (C$_1$–C$_6$)alkylthio or mercapto(C$_1$–C$_6$)alkyl, oxo, nitro, cyano halo —COOH, or —COOR$^A$, —CONH$_2$, —CONHR$^A$, or —CONR$^A$R$^B$

—COR$^A$, —SO$_2$R$^A$,

—NHCOR$^A$,

—NH$_2$, —NHR$^A$, or —NR$^A$R$^B$, wherein R$^A$ and R$^B$ are independently a (C$_1$–C$_6$) alkyl group, R$^A$ and R$^B$ taken together with the nitrogen atom to which they are attached form a 5- or 6-membered heterocyclic ring which may be substituted by (C$_1$–C$_3$)alkyl, hydroxy, or hydroxy(C$_1$–C$_3$)alkyl.

The amino group A may also be one of formula —NR$_6$R$_7$ wherein R$_6$ and R$_7$ when taken together with the nitrogen atom to which they are attached form a saturated heterocyclic ring of 5 to 8 atoms optionally fused to a saturated or unsaturated carbocyclic or heterocyclic second ring of 5 to 7 ring atoms, any of which rings being optionally substituted by a radical of formula (II) as defined above. Examples of cyclic amino groups are 1-pyrrolidinyl, piperidin-1-yl, 1-piperazinyl, hexahydro-1-pyridazinyl, morpholin-4-yl, tetrahydro-1,4-thiazin-4-yl, tetrahydro-1,4-thiazin4-yl 1-oxide, tetrahydro-1,4-thiazin-4-yl 1,1-dioxide, hexahydroazipino, thiomorpholino, diazepino, and thiazolidinyl. Presently preferred are piperidin-1-yl and 1-piperazinyl.

The Group of Formula (II)

In the substituent (II) Alk$^1$ and Alk$^2$ may independently represent, for example —(CH$_2$)— or —(CH$_2$CH$_2$)—. In the case where m is 0 and p is 1, X may be, for example —S—, —S(=O)—, or preferably —C(=O)— or —S(O$_2$)—. In such cases n may be 0 or 1, and when A is a cyclic amino group which contains a second ring nitrogen, the X radical may be linked to that ring nitrogen, for example (in the case of X=—C(=O)— or —S(O$_2$)—) as an amide or sulphonamide bond.

In the substituent (II) m, n and p may all be 0, so that the group Z is directly linked to the amino group A.

In a preferred subset of the compounds of the invention, the substituent (II) has the formula —CH$_2$Z, —OZ, or —(C=O)Z wherein Z is C$_1$-C$_3$ alkyl, phenyl, 3,4-methylenedioxyphenyl, morpholinyl, pyrimidinyl, 1,2,3-thiadiazolyl, 1,4-thiazolyl, benzofuranyl, furanyl, thienyl, pyranyl, pyrrolyl, pyrazolyl, isoxazolyl, or pyridyl, any of which may optionally be substituted as specified. In particular, Z may be a methyl, ethyl, n- or iso-propyl, phenyl, 3,4-methylenedioxyphenyl, morpholinyl, pyrimidin-2-yl, 1,2,3-thiadiazol-5-yl, 1,4-thiazol-5-yl, benzofuran-2-yl, 2-or 3-furanyl, 2- or 3-thienyl, 2- or 3-pyranyl, 2-, 3- or 4-pyrrolyl, 3-, 4- or 5-pyrazolyl, 3-, 4- or 5-isoxazolyl, or 2-, 3- or 4-pyridyl ring any of which may optionally be substituted as specified in the broad description of the compounds of the invention.

Compounds of the invention include those selected from the group consisting of compounds of formulae (IIA) or (IIB).

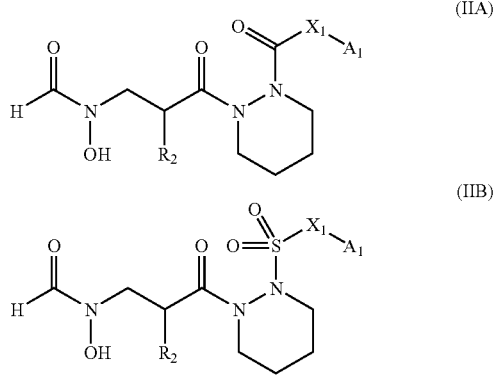

wherein R$_2$ is as defined in relation to formula (II), especially n-propyl, n-butyl, n-pentyl, cyclopentylmethyl, cyclopentylethyl, cyclohexylmethyl or cyclohexylethyl;

X$_1$ is a bond, C$_1$-C$_3$ alkylene, —NH— or —O—; and

A$_1$ is optionally substituted C$_1$-C$_6$ alkyl, cycloalkyl, aryl, or heterocyclic, for example methyl, ethyl phenyl, cyclopentyl, cyclohexyl, 2- or 3-furanyl, 2- or 3- thienyl, 2-, 3- or 4-pyridyl, 3-, 4- or 5-pyrazolyl, 3-, 4- or 5-oxazolyl, or 3-, 4- or 5-thiazolyl, methoxymethyl, 3,5bis-(trifluoromethyl) phenyl, 4-trifluoromethylphenyl, 4-methoxyphenyl, 3,4-methylenedioxyphenyl, 4-fluorophenyl benzyl, 3-pyridyl, 4-pyridyl, cyclohexyl, 1,3-dimethylpyrazol-5-yl, 1-methylimidazol-5-yl, and 2-[morpholin-1-yl]pyrid-5-yl.

Particular compounds of the invention include those of the Examples herein.

In general, compounds of the invention are accessible by conventional synthetic procedures, for example by acylation of cyclic diazole compund (IV) with an activated derivative of an acid (III),

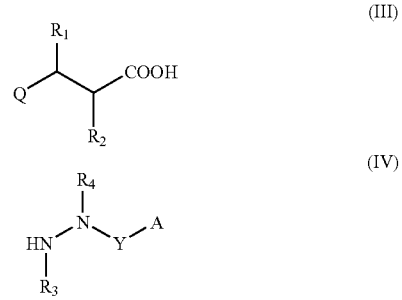

by methods known from peptide synthesis for example using an acid chloride, wherein the NH and/or OH groups in Q are protected during the acylation and deprotected thereafter. Other compounds of the invention may be prepared by reaction of a compound of formula (V) with a chloride of formula (VI) or an isocyanate of formula (VII):

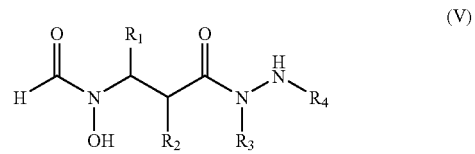

The Examples herein provide further details of routes and methods for the preparation of compounds of the invention.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate embodiments of the invention.:

In the Examples, the following abbreviations have been used:

| | |
|---|---|
| DMF | Dimethylformamide |
| HOBt | 1-Hydroxybenzotriazole |
| HPLC | High performance liquid chromatography |
| LRMS | Low resolution mass spectrometry |
| NMR | Nuclear magnetic resonance |
| RT | Retention Time |
| TLC | Thin layer chromatography |
| DIEA | N,N-diisopropylethylamine |
| DCM | Dichloromethane |
| HATU | O-(7-Azabenzotriazo-1-yl)-N,N,N',N'-tetramethyluronium hexafluorophosphate |

$^1$H and $^{13}$C NMR spectra were recorded using a Bruker DPX 250 spectrometer at 250.1 and 62.9 MHz, respectively. Mass spectra were obtained using a Perkin Elmer Sciex API 165 spectrometer using both positive and negative ionisation modes. Infra-red spectra were recorded on a Perkin Elmer PE 1600 FTIR spectrometer. Analytical HPLC was performed on a Beckman System Gold, using Waters Nova Pak C18 column (150 mm, 3.9 mm) with 20 to 90% solvent B gradient (1 ml/min) as the mobile phase. [Solvent A: 0.05% TFA in 10% water 90% methanol; Solvent B: 0.05% TFA in 10% methanol 90%], detection wavelength at 230 nm. Preparative HPLC was performed on a Gilson autoprep instrument using a C18 Waters delta prep-pak cartridge (15 μm, 300 A, 25 mm, 10 mm) with 20 to 90% solvent B gradient (6 ml/min) as the mobile phase. [Solvent A water, Solvent B: methanol], UV detection was at 230 nm.

EXAMPLE 1

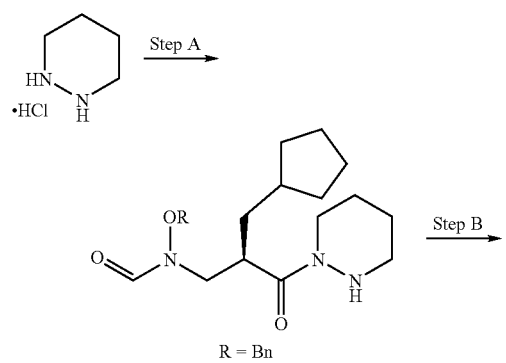

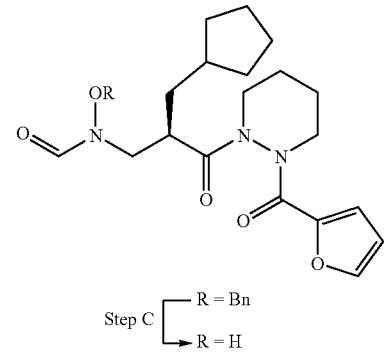

Step A. 3-Benzyloxyformylamino-(2R)-cyclopentylmethyl-propionic acid, EDAC, HOBt, DMF, 0° C. to rt, 5 h;
Step B. 2-furoyl chloride, DIEA, CH$_2$Cl$_2$, 0° C. to rt, 16 h;
Step C. H$_2$ (g), 10% Pd/C, MeOH, rt, 2 h.

Step A:

N-Benzyloxy-N-[(2R)-cyclopentylmethyl-3-oxo-3-(tetrahydropyridazin-1-yl)propyl]formamide To a solution of 3-benzyloxyformylamino-(2R)-cyclopentylmethyl-propionic acid (3.73 g, 12.2 mmol) in DMF (40 ml) at 0° C. under argon was added EDAC (2.58 g, 13.5 mmol) and HOBt (0.83 g, 6.12 mmol). The resulting mixture was stirred for 15 min at 0° C. before 1,2-diazacyclohexane hydrochloride (1.50 g, 12.2 mmol) was introduced followed by DIEA (4.69 ml, 27.0 mmol) in DMF (5 ml). The reaction was maintained at 0° C. for 1 h and then warmed to rt where it was left for 5 h. After this time, the reaction was diluted with EtOAc and washed with 1M Na$_2$CO$_3$. The aqueous phase was removed and extracted with additional EtOAc (×1). The combined organic fractions were washed with H$_2$O and sat. NaCl and then separated, dried (MgSO$_4$), filtered and concentrated under reduced pressure. The crude material was purified by chromatography on silica eluting with 100% EtOAc. This gave the title compound as a colourless oil (2.95 g, 65%). 1H-NMR; δ (CD$_3$OD), 8.18 (0.5H, s, CHO), 7.88 (0.5H, s, CHO), 7.50–7.30 (5H, m, ArH), 4.92–4.65 (2H, br m, CH$_2$Ph), 4.10–2.80 (7H, m), 1.75–1.40 (13H, m), 1.20–1.00 (2H, m). LRMS: +ve ion: 396 [M+23], 374 [M+1], 346.

Step B:

N-Benzyloxy-N-{(2R)-cyclopentylmethyl-3-[2-(furan-2-Carbonyl)-tetrahydropyridazin-1-yl]-3-oxo-propyl}formamide To a solution of N-benzyloxy-N-[(2R)-cyclopentylmethyl-3-oxo-3-(tetrahydropyridazin-1-yl)propyl]formamide (60 mg, 0.16 mmol) in DCM (1 ml) at 0° C. under argon was added 2-furoyl chloride (17 μl, 0.17 mmol) followed by DIEA (34 μl, 0.19 mmol). The mixture was stirred for 30 min at 0° C. and then warmed to rt where it was maintained for 16 h. After this time the reaction was diluted with EtOAc and washed with 1M citric acid, sat. NaHCO$_3$ and sat. NaCl. The organic layer was dried (MgSO$_4$), filtered and concentrated under reduced pressure. The crude material was purified by chromatography on silica eluting with 70–100% EtOAc/hexanes. This gave the title compound as a colourless oil (67 mg, 89%). 1H-NMR; δ (CD$_3$OD), 8.26 (0.33H, s, CHO), 7.95 (0.67H, s, CHO), 7.78 (1H, br s, HetArH), 7.50–7.25 (5H, m, ArH), 7.03 (1H, br m, HetArH), 6.63–6.52 (1H, br m, HetArH), 5.03–4.70 (2H, br m, CH₂Ph), 4.70–4.40 (2H, m), 4.30–2.85 (5H, m), 1.90–1.00 (13H, m), 0.95–0.60 (2H, m). LRMS: +ve ion: 490 [M+23].

Step C:

(2R)-Cyclopentylmethyl-3-[2-(furan-2-Carbonyl)-tetrahydropyridazin-1-yl]-3-oxo-propyl}formamide To a solution of the N-benzyloxy-N-{(2R)-cyclopentylmethyl-3-[2-(furan-2-Carbonyl)-tetrahydropyridazin-1-yl]-3-oxo-propyl}formamide (65 mg, 0.14 mmol) in MeOH (3 ml) at rt under argon was added 10% Pd/C (8 mg). Hydrogen gas was bubbled through the black suspension for 15 min and then the reaction was left under an atmosphere of hydrogen for 2 h. After this time, the suspension was filtered and the collected solids were washed with additional MeOH. The combined filtrate and washings were concentrated under reduced pressure to give the title compound as a colourless solid (52 mg, 100%). 1H-NMR; δ (CD₃OD), 8.29 (0.33H, s, CHO), 7.89 (0.67H, s, CHO), 7.78 (1H, br s, HetArH), 7.20–7.00 (1H, br m, HetArH), 6.64 (1H, br m, HetArH), 4.70–4.55 (2H, m), 3.95–2.95 (5H, m), 1.95–1.0 (13H, m), 0.95–0.80 (2H, m). LRMS: +ve ion: 400 [M+23]. HPLC Rt=4.49 min (214 nm).

The compounds of the following Examples 2–12 were prepared by method of Example 1:

EXAMPLE 2

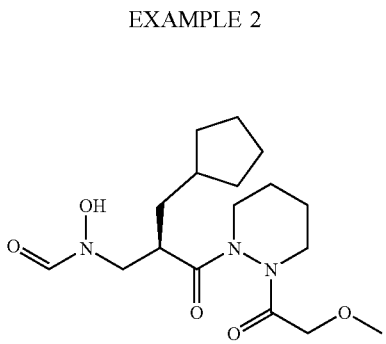

N-{(2R)-Cyclopentylmethyl-3-[2-(2-methoxyacetyl)tetrahydropyridazin-1-yl]-3-oxo-propyl}-N-hydroxyformamide LRMS: +ve ion: 378 [M+23]. HPLC Rt=4.61 and 4.64 min [rotamers] (214 nm).

EXAMPLE 3

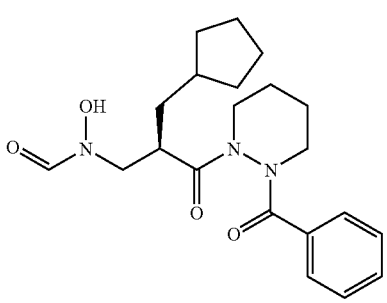

N-{(2R)-Cyclopentylmethyl-3-[2-benzoyl-tetrahydropyridazin-1-yl]-3-oxo-propyl}-N-hydroxyformamide LRMS: +ve ion: 410 [M+23], 191. HPLC Rt=5.24 min (214 nm).

EXAMPLE 4

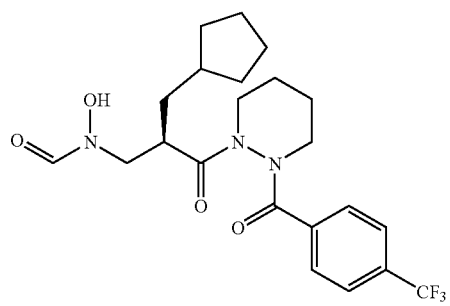

N-{(2R)-Cyclopentylmethyl-3-[2-(4-trifluoromethylbenzoyl)-tetrahydropyridazin-1-yl]-3-oxo-propyl}-N-hydroxyformamide LRMS: +ve ion: 478 [M+23], 259. HPLC Rt=5.47 min (214 nm).

EXAMPLE 5

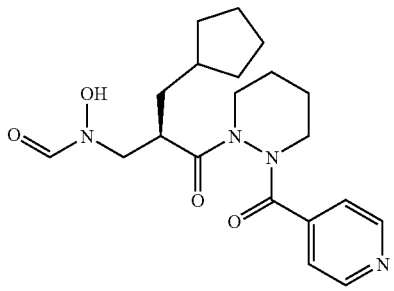

N-{(2R)-Cyclopentylmethyl-3-[2-(pyridine-4-Carbonyl)-tetrahydropyridazin-1-yl]-3-oxo-propyl}-N-hydroxyformamide LRMS: +ve ion: 411 [M+23], 389 [M+1], 192. HPLC Rt=1.00 min (214 nm).

EXAMPLE 6

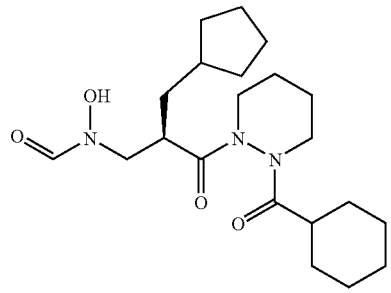

N-{(2R)-Cyclopentylmethyl-3-[2-Cyclohexanecarbonyl-tetrahydropyridazin-1-yl]-3-oxo-propyl}-N-hydroxyformamide LRMS: +ve ion: 416 [M+23], 197. HPLC Rt=5.29 min (214 nm).

EXAMPLE 7

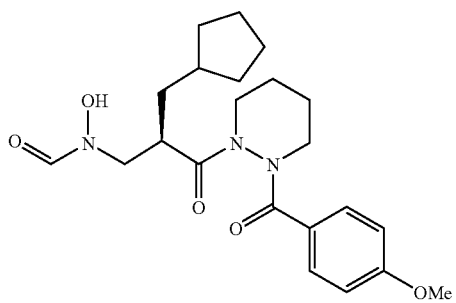

N-{(2R)-Cyclopentylmethyl-3-[2-(4-methoxybenzoyl)-tetrahydropyridazin-1-yl]-3-oxo-propyl}-N-hydroxyformamide
LRMS: +ve ion: 440 [M+23], 221. HPLC Rt=4.91 min (214 nm).

EXAMPLE 8

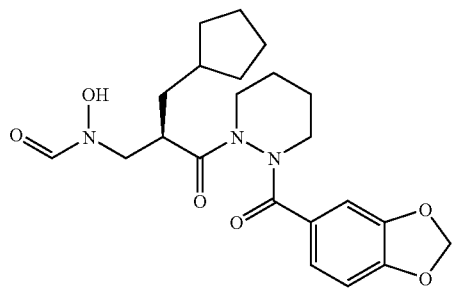

N-{(2R)-Cyclopentylmethyl-3-[2-(benzo[1,3]dioxole-5carbonyl)-tetrahydropyridazin-1-yl]-3-oxo-propyl}-N-hydroxyformamide
LRMS: +ve ion: 454 [M+23], 235. HPLC Rt=4.84 min (214 nm).

EXAMPLE 9

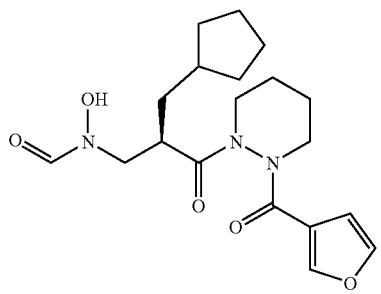

N-{(2R)-Cyclopentylmethyl-3-[2-(furan-3-Carbonyl)-tetrahydropyridazin-1-yl]-3-oxo-propyl}-N-hydroxyformamide
LRMS: +ve ion: 400 [M+23], 181.

EXAMPLE 10

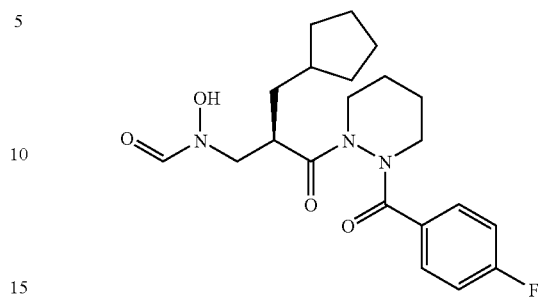

N-{(2R)-Cyclopentylmethyl-3-[2-(4-fluorobenzoyl)-tetrahydropyridazin-1-yl]-3-oxo-propyl}-N-hydroxyformamide
LRMS: +ve ion: 428 [M+23], 209. HPLC Rt=5.01 min (214 nm).

EXAMPLE 11

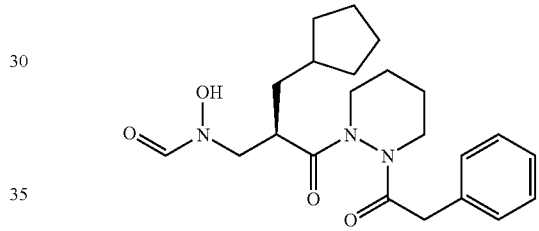

N-{(2R)-Cyclopentylmethyl-3-[2-phenylacetyl-tetrahydropyridazin-1-yl]-3-oxo-propyl}-N-hydroxyformamide
LRMS: +ve ion: 424 [M+23], 205. HPLC Rt 5.15 and 5.25 min [rotamers] (214 nm).

EXAMPLE 12

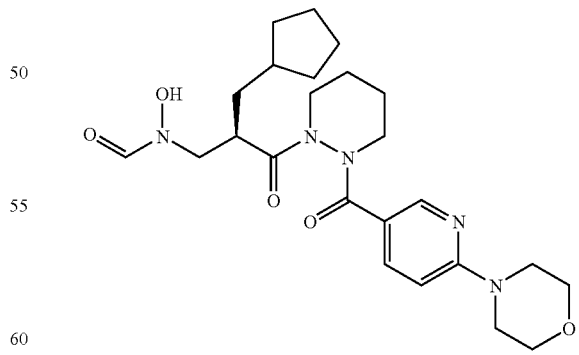

N-{(2R)-Cyclopentylmethyl-3-[2-(6-morpholin-4-yl-pyridine-3-Carbonyl)-tetrahydropyridazin-1-yl]-3-oxo-propyl}N-hydroxyformamide
LRMS: +ve ion: 496 [M+23], 474 [M+1], 277, 191. HPLC Rt=1.84 min (214 nm).

EXAMPLE 13

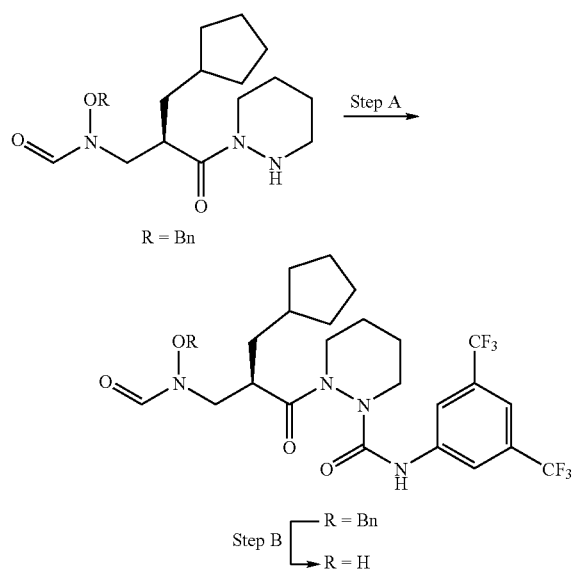

Step A. 3,5-Bis-(trifluoromethyl)phenyl isocyanate, EtOAc, rt, 16 h; Step B. $H_2$ (g), 10% Pd/C, MeOH, rt, 2 h.

Step A:

2-[3-(Benzyloxyformylamino)-(2R)-cyclopentylmethyl-propionyl]-tetrahydropyridazine-1-Carboxylic acid (3,5-bis-(trifluoromethyl)phenyl)amide To a solution of N-benzyloxy-N-[(2R)-cyclopentylmethyl-3-oxo-3-(tetrahydropyridazin-1-yl)propyl]formamide (53 mg, 0.14 mmol) in EtOAc (2 ml) at rt under argon was added 3,5-bis-(trifluoromethyl)phenyl isocyanate (36 mg, 0.14 mmol). The resulting mixture was stirred for 16 h at rt and then concentrated under reduced pressure. The crude product was purified by chromatography on silica eluting with 70–100% EtOAc/hexanes to give the title compound as a colourless oil (76 mg, 85%). 1H-NMR; δ ($CD_3OD$), 8.25–7.88 (3H, m, ArH and CHO), 8.60–7.20 (6H, m, ArH), 5.01–4.75 (2H, m, $CH_2Ph$), 4.60–2.90 (7H, m), 1.80–1.05 (13H, m), 1.00–0.90 (2H, m). LRMS: +ve ion: 651 [M+23], 400.

Step B:

2-[(2R)-Cyclopentylmethyl-3-(formylhydroxyamino)-propionyl]-tetrahydropyridazine-1-Carboxylic acid (3,5-bis-(trifluoromethyl)phenyl)amide To a solution of the 2-[3-(benzyloxyformylamino)-(2R)-cyclopentylmethyl-propionyl]-tetrahydropyridazine-1-Carboxylic acid (3,5-bis-(trifluoromethyl) phenyl)amide (75 mg, 0.12 mmol) in MeOH (4 ml) at rt under argon was added 10% Pd/C (10 mg). Hydrogen gas was bubbled through the black suspension for 15 min and then the reaction was left under an atmosphere of hydrogen for 2 h. After this time, the suspension was filtered and the collected solids were washed with additional MeOH. The combined filtrate and washings were concentrated under reduced pressure to give the title compound as a colourless solid (63 mg, 98%). 1H-NMR; δ ($CD_3OD$), 8.30–8.24 (2.5H, m, ArH and CHO), 7.91 (0.5H, s, CHO), 7.62 (1H, s, ArH), 4.60–4.38 (2H, m), 4.10–2.85 (5H, m), 1.90–1.05 (13H, m), 1.00–0.90 (2H, m). LRMS: +ve ion: 561 [M+23]. HPLC Rt=6.30 min (214 nm).

The compounds of Examples 14 to 20 were prepared by methods analogous to that of Example 2 substituting the appropriate isocyanate for that used in Example 13

EXAMPLE 14

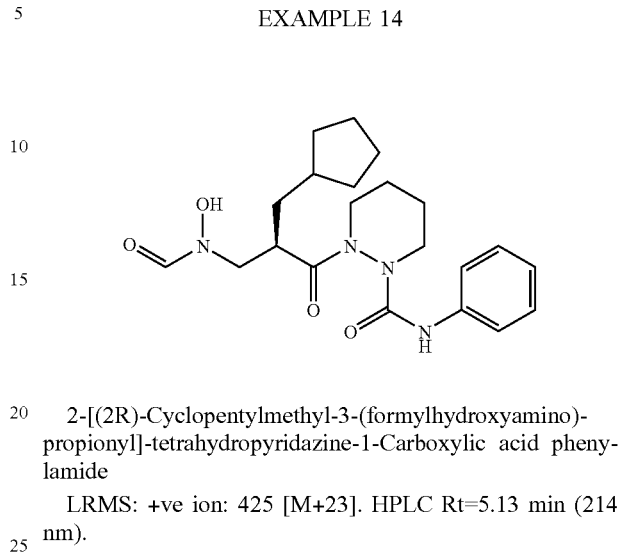

2-[(2R)-Cyclopentylmethyl-3-(formylhydroxyamino)-propionyl]-tetrahydropyridazine-1-Carboxylic acid phenylamide LRMS: +ve ion: 425 [M+23]. HPLC Rt=5.13 min (214 nm).

EXAMPLE 15

2-[(2R)-Cyclopentylmethyl-3-(formylhydroxyamino)-propionyl]-tetrahydropyridazine-1-Carboxylic acid (3-methoxyphenyl)amide LRMS: +ve ion: 455 [M+23]. HPLC Rt=5.13 min (214 nm).

EXAMPLE 16

2-[(2R)-Cyclopentylmethyl-3-(formylhydroxyamino) propionyl]-tetrahydropyridazine-1-Carboxylic acid (4-fluorophenyl)amide LRMS: +ve ion: 443 [M+23]. HPLC Rt=5.22 min (214 nm).

EXAMPLE 17

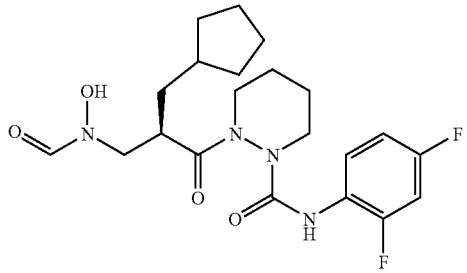

2-[(2R)-Cyclopentylmethyl-3-(formylhydroxyamino)-propionyl]-tetrahydropyridazine-1-Carboxylic acid (2,4-bis(fluoro)phenyl)amide LRMS: +ve ion: 461 [M+23]. HPLC Rt=5.15 min (214 nm).

EXAMPLE 18

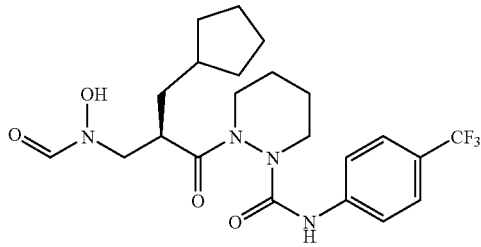

2-[(2R)-Cyclopentylmethyl-3-(formylhydroxyamino)-propionyl]-tetrahydropyridazine-1-Carboxylic acid (4-trifluoromethylphenyl)amide LRMS: +ve ion: 493 [M+23]. HPLC Rt=5.81 min (214 nm).

EXAMPLE 19

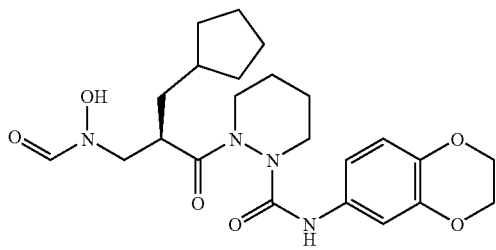

2-[(2R)-Cyclopentylmethyl-3-(formylhydroxyamino)-propionyl]-tetrahydropyridazine-1-Carboxylic acid (2,3,4a,8a-tetrahydrobenzo[1,4]dioxin-6-yl)amide LRMS: +ve ion: 483 [M+23]. HPLC Rt=4.96 min (214 nm).

EXAMPLE 20

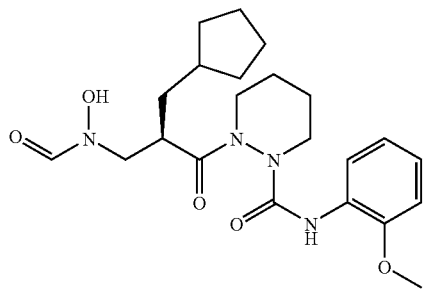

2-[(2R)-Cyclopentylmethyl-3-(formylhydroxyamino)-propionyl]-tetrahydropyridazine-1-Carboxylic acid (2-methoxyphenyl)amide LRMS: +ve ion: 455 [M+23]. HPLC Rt=5.27 and 5.37 min [rotamers] (214 nm).

EXAMPLE 21

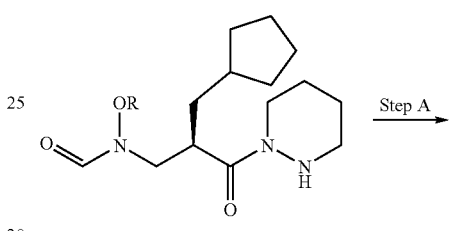

R = Bn

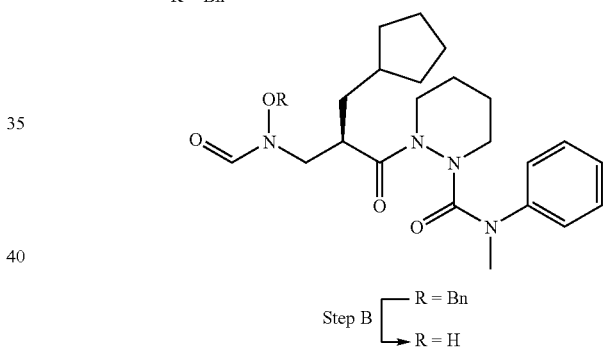

Step B $\begin{bmatrix} R = Bn \\ R = H \end{bmatrix}$

Step A. N-Methyl-N-phenyl carbamoyl chloride, THF, DIEA, microwave irradiation (100 W), 140° C., 12 min; Step B. H$_2$ (g), 10% Pd/C, MeOH, rt, 1 h.

Step A:
2-[3-(Benzyloxyformylamino)-(2R)-cyclopentylmethyl-propionyl]-tetrahydropyridazine-1-Carboxylic acid methylphenylamide To a solution of N-benzyloxy-N-[(2R)-cyclopentylmethyl-3-oxo-3-(tetrahydropyridazin-1-yl)propyl]formamide (65 mg, 0.174 mmol) in THF containing DIEA (33 μl, 0.19 mmol) at rt in air was added N-methyl-N-phenyl carbamoyl chloride (30 mg, 0.174 mmol). The mixture was then irradiated with microwaves (100 W) at 140° C. for 12 min. After this time the reaction was concentrated under reduced pressure and the crude product was purified by preparative HPLC to give the product as a colourless solid (8 mg, 7%).

LRMS: +ve ion: 529 [M+23], 396.

Step B:
2-[(2R)-Cyclopentylmethyl-3-(formylhydroxyamino)-propionyl]-tetrahydropyridazine-1-Carboxylic acid methylphenylamide To a solution of 2-[3-(benzyloxyformylamino)-(2R)-cyclopentylmethyl-propionyl]-tetrahydropyridazine-1-Carboxylic acid methylphenylamide (6 mg, 0.08 mmol) in MeOH (1 ml) at rt under argon was added 10% Pd/C (1 mg). Hydrogen gas was bubbled through the black suspension for 15 min and then the reaction was left under an atmosphere of hydrogen for 1 h. After this time, the suspension was filtered and the collected solids were washed with additional MeOH. The combined filtrate and washings were concentrated under reduced pressure to give the title compound as a colourless solid (2 mg, 41%). LRMS: +ve ion: 439 [M+23], 239. HPLC Rt=5.62 min (214 nm).

The compound of Example 22 was prepared by the method of Example 21 of Example 10 substituting the appropriate carbamoyl chloride for that used in Example 21

EXAMPLE 22

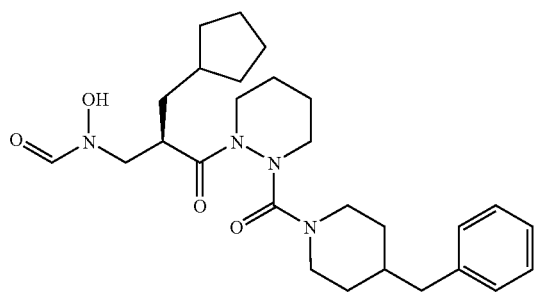

N-{(2R)-Cyclopentylmethyl-3-[2-(4-benzylpiperidine-1-Carbonyl)-tetrahydropyridazin-1-yl]-3-oxo-propyl}-N-hydroxyformamide LRMS: +ve ion: 507 [M+23], 485 [M+1], 310, 249, 176. HPLC Rt=5.90 and 6.32 min [rotamers] (214 nm).

EXAMPLE 23

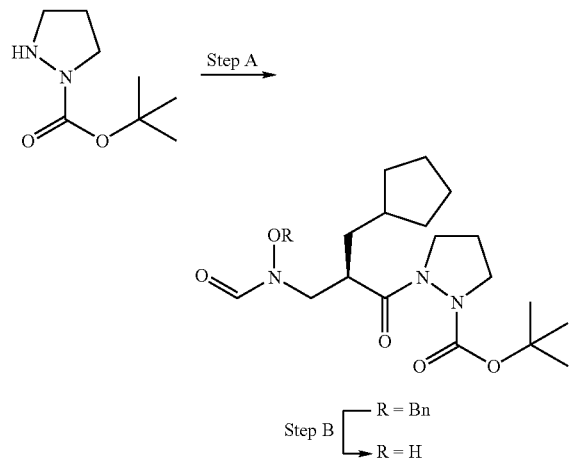

Step A. 3-Benzyloxyformylamino-(2R)-cyclopentylmethyl-propionic acid, HATU, DIEA, DMF, 0° C. to rt, 2.5 h; Step B. H$_2$ (g), 10% Pd/C, MeOH, rt, 2 h.

Step A:

2-[3-(Benzyloxyformylamino)-(2R)-cyclopentylmethyl-propionyl]-pyrazolidine-1-Carboxylic acid tert-butyl ester To a solution of 3-benzyloxyformylamino-(2R)-cyclopentylmethyl-propionic acid (103 mg, 0.34 mmol) in DMF (2 ml) at 0° C. under argon was added HATU (128 mg, 0.34 mmol) and DIEA (70 μl, 0.41 mmol). The resulting mixture was stirred for 10 min before a solution of N-tert-(butoxycarbonyl)-1,2-diazacyclopentane (58 mg, 0.34 mmol) in DMF (0.5 ml) was introduced. After 1 h at 0° C., the reaction was warmed to rt where it was maintained for 1.5 h. The mixture was then diluted with EtOAc and washed with 1M citric acid, 1M Na$_2$CO$_3$ and sat. NaCl. The organic layer was dried (MgSO$_4$), filtered and concentrated under reduced pressure. The crude product was purified by chromatography on silica eluting with 50–70% EtOAc/hexanes to give the title compound as a colourless oil (46 mg, 30%). 1H-NMR; δ (CDCl$_3$), 8.23 (0.25H, s, CHO), 8.08 (0.25H, s, CHO), 7.99 (0.25 H, s, CHO), 7.85 (0.25H, s, CHO), 7.45–7.26 (5H, m, ArH), 4.87–4.60 (2H, br m, CH$_2$Ph), 4.20–2.80 (7H, m), 2.10–1.40 (11H, m), 1.45 (9H, s, (CH$_3$)$_3$), 1.20–1.00 (2H, m). LRMS: +ve ion: 482 [M+23], 382.

Step B:

2-[(2R)-Cyclopentylmethyl-3-(formylhydroxyamino)-propionyl]-pyrazolidine-1-Carboxylic acid tert-butyl ester To a solution of 2-[3-(benzyloxyformylamino)-(2R)-cyclopentylmethyl-propionyl]-pyrazolidine-1-Carboxylic acid tert-butyl ester (46 mg, 0.10 mmol) in MeOH (4 ml) at rt under argon was added 10% Pd/C (8 mg). Hydrogen gas was bubbled through the black suspension for 15 min and then the reaction was left under an atmosphere of hydrogen for 2 h. After this time, the suspension was filtered and the collected solids were washed with additional MeOH. The combined filtrate and washings were concentrated under reduced pressure to give the title compound as a colourless solid (36 mg, 97%). 1H-NMR; δ (CD$_3$OD), 8.28 (0.25H, s, CHO), 8.22 (0.25H, s, CHO), 7.93 (0.25H, s, CHO), 7.80 (0.25H, s, CHO), 4.20–3.79 (4H, m), 3.78–3.40 (1H, m), 3.39–3.02 (2H, m), 2.20–1.40 (11H, m), 1.51 (4.5H, s, (CH$_3$)$_3$), 1.50 (4.5H, s, (CH$_3$)$_3$),1.20–1.01 (2H, m). LRMS: +ve ion: 392 [M+23], 292, 270. HPLC Rt=5.23 min (214 nm).

The compound of Example 24 was prepared by a method analogous to that to Example 23:

EXAMPLE 24

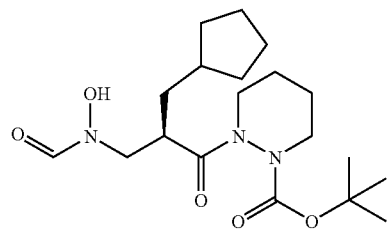

2-[(2R)-Cyclopentylmethyl-3-(formylhydroxyamino)-propionyl]-tetrahydropyridazine-1-Carboxylic acid tert-butyl ester 1H-NMR; δ (CD$_3$OD), 8.26 (0.25H, s, CHO), 7.91 (0.25H, s, CHO), 7.84 (0.5H, s, CHO), 4.44–4.40 (1H, m), 4.22–3.10 (4H, m), 3.10–2.70 (2H, m), 1.85–1.30 (13H, m), 1.51 (4.5H, s, (CH$_3$)$_3$), 1.50 (4.5H, s, (CH$_3$)$_3$), 1.20–1.00 (2H, m). LRMS: +ve ion: 406 [M+23], 306. HPLC Rt=5.41 and 5.55 min [rotamers] (214 nm).

EXAMPLE 25

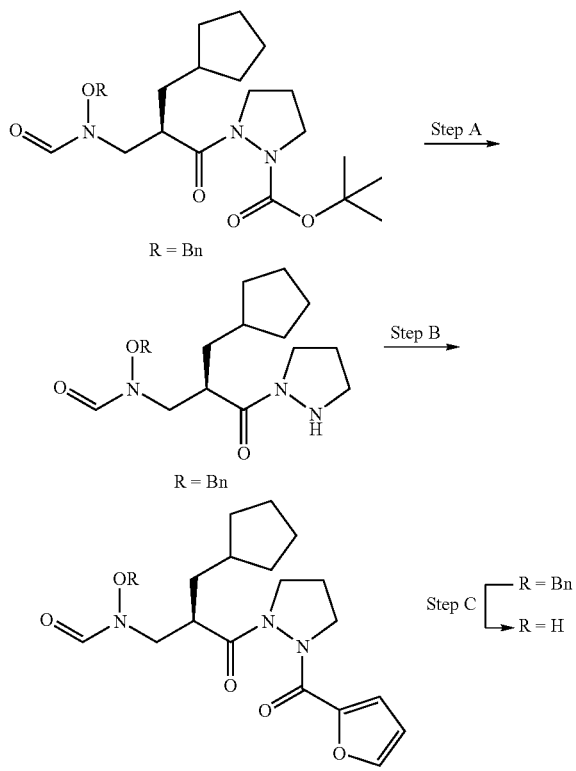

Step A. BF$_3$.Et$_2$O, CH$_2$Cl$_2$:AcOH (5:1), 0° C. 2 h; Step B. 2-furoyl chloride, DIEA, CH$_2$Cl$_2$, 0° C. to rt, 1 h; Step C. H$_2$ (g), 10% Pd/C, MeOH, rt, 1 h.

Step A:
N-Benzyloxy-N-[(2R)-cyclopentylmethyl-3-oxo-3-pyrazolidin-1-yl-propyl]formamide To a solution of 2-[3-(benzyloxyformylamino)-(2R)-cyclopentylmethyl-propionyl]-pyrazolidine-1-Carboxylic acid tert-butyl ester (477 mg, 1.04 mmol) in DCM (12.5 ml) at 0° C. under argon was added glacial acetic acid (2.5 ml) followed by boron trifluoride etherate (0.77 ml, 6.24 mmol). The solution was stirred at 0° C. for 2 h and then diluted with EtOAc. The mixture was washed with 1M Na$_2$CO$_3$ and sat. NaCl. The organic layer was dried (MgSO$_4$), filtered and concentrated under reduced pressure to give the title compound which was used without further purification. 1H-NMR; δ (CDCl$_3$), 8.19 (0.5H, s, CHO), 7.88 (0.5H, s, CHO), 7.47–7.26 (5H, m, ArH), 4.95–4.60 (2H, br m, CH$_2$Ph), 3.93–3.30 (5H, m), 3.20–2.80 (2H, m), 2.00–1.40 (12H, m), 1.15–1.00 (2H, m). LRMS: +ve ion: 382 [M+23], 332.

Step B:
N-Benzyloxy-N-{(2R)-cyclopentylmethyl-3-[2-(furan-2-Carbonyl)-pyrazolidin-1-yl]-3-oxo-propyl}formamide To a solution of N-benzyloxy-N-[(2R)-cyclopentylmethyl-3-oxo-3-pyrazolidin-1-yl-propyl]formamide (31 mg, 0.086 mmol) in DCM (2 ml) at 0° C. under argon was added 2-furoyl chloride (9 μl, 0.095 mmol) followed by DIEA (18 μl, 0.104 mmol). The mixture was stirred for 30 min at 0° C. and then warmed to rt where it was maintained for 1 h. After this time the reaction was diluted with EtOAc and washed with 1M citric acid, sat. NaHCO$_3$ and sat. NaCl. The organic layer was dried (MgSO$_4$), filtered and concentrated under reduced pressure. The crude material was purified by chromatography on silica eluting with 80% EtOAc/hexanes. This gave the title compound as a colourless oil (34 mg, 87%). 1H-NMR; δ (CD$_3$OD), 8.32 (0.25H, s, CHO), 8.10 (0.25H, s, CHO), 7.96 (0.25H, s, CHO), 7.90 (0.25H, s, CHO), 7.80–7.74 (1H, br m, HetArH), 7.50–7.20 (6H, br m, ArH and HetArH), 6.60 (1H, br s, HetArH), 5.00–4.80 (2H, br m, CH$_2$Ph), 4.40–2.95 (7H, m), 2.20–1.40 (11H, m), 1.20–0.85 (2H, m). LRMS: +ve ion: 476 [M+23].

Step C:
(2R)-Cyclopentylmethyl-3-[2-(furan-2-Carbonyl)-pyrazolidin-1-yl]-3-oxo-propyl}formamide To a solution of the N-benzyloxy-N-{(2R)-cyclopentylmethyl-3-[2-(furan-2-Carbonyl)-pyrazolidin-1-yl]-3-oxo-propyl}formamide (32 mg, 0.071 mmol) in MeOH (2 ml) at rt under argon was added 10% Pd/C (5 mg). Hydrogen gas was bubbled through the black suspension for 15 min and then the reaction was left under an atmosphere of hydrogen for 1 h. After this time, the suspension was filtered and the collected solids were washed with additional MeOH. The combined filtrate and washings were concentrated under reduced pressure to give the title compound as a colourless solid (23 mg, 90%). 1H-NMR; δ (CD$_3$OD), 8.28 (0.25H, s, CHO), 8.22 (0.25H, s, CHO), 7.90–7.70 (1.5H, m, CHO and HetArH), 7.30–7.20 (1H, br m, HetArH), 6.65 (1H, br s, HetArH), 4.40–3.05 (7H, m), 2.25–1.30 (11H, m), 1.20–0.85 (2H, m). LRMS: +ve ion: 386 [M+23]. HPLC Rt=4.36 min (214 nm).

The compounds of Examples 26–37 were prepared by the method of Example 25:

EXAMPLE 26

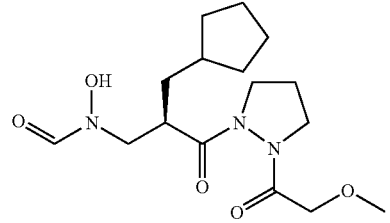

N-{(2R)-Cyclopentylmethyl-3-[2-(2-methoxyacetyl)-pyrazolidin-1-yl]-3-oxo-propyl}N-hydroxyformamide
LRMS: +ve ion: 364 [M+23], 167. HPLC Rt=2.39 min (214 nm).

EXAMPLE 27

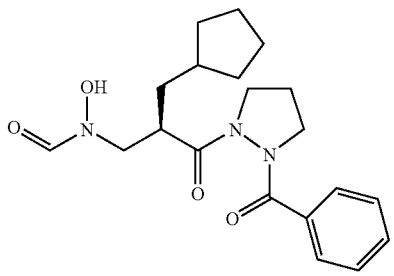

N-{(2R)-Cyclopentylmethyl-3-[2-benzoyl-pyrazolidin-1-yl]-3-oxo-propyl}-N-hydroxyformamide LRMS: +ve ion: 396 [M+23], 177. HPLC Rt=4.72 min (214 nm).

EXAMPLE 28

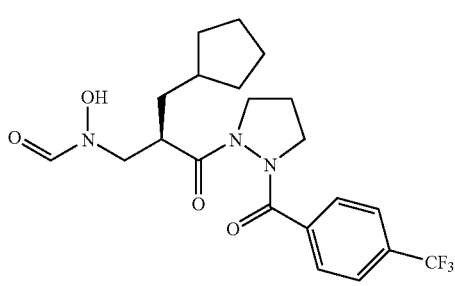

N-{(2R)-Cyclopentylmethyl-3-[2-(4-trifluoromethylbenzoyl)-pyrazolidin-1-yl]-3-oxo-propyl}-N-hydroxyformamide LRMS: +ve ion: 464 [M+23], 245. HPLC Rt=5.36 min (214 nm).

EXAMPLE 29

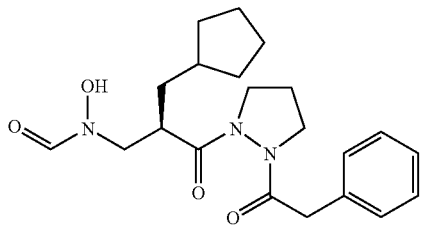

N-{(2R)-Cyclopentylmethyl-3-[2-phenylacetyl-pyrazolidin-1-yl]-3-oxo-propyl}-N-hydroxyformamide LRMS: +ve ion: 410 [M+23], 191. HPLC Rt=4.97 min (214 nm).

EXAMPLE 30

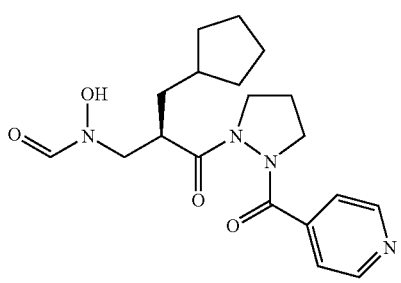

N-{(2R)-Cyclopentylmethyl-3-[2-(pyridine-4-Carbonyl)-pyrazolidin-1-yl]-3-oxo-propyl}-N-hydroxyformamide LRMS: +ve ion: 397 [M+23], 178. HPLC Rt=0.99 min (214 nm).

EXAMPLE 31

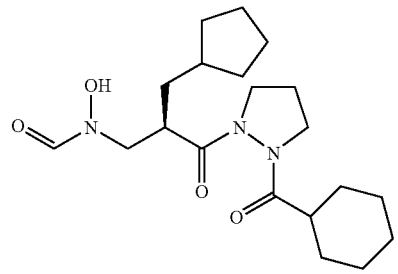

N-{(2R)-Cyclopentylmethyl-3-[2-Cyclohexanecarbonyl-pyrazolidin-1-yl]-3-oxo-propyl}-N-hydroxyformamide LRMS: +ve ion: 402 [M+23], 183. HPLC Rt=5.16 min (214 nm).

EXAMPLE 32

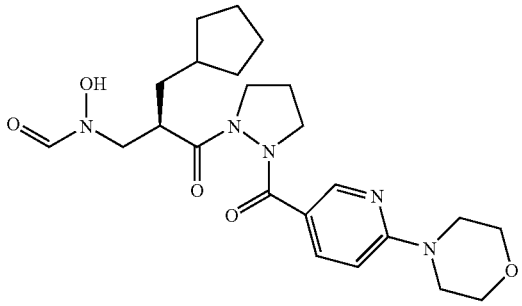

N-{(2R)-Cyclopentylmethyl-3-[2-(6-morpholin-4-yl-pyridine-3-Carbonyl)-pyrazolidin-1-yl]-3-oxo-propyl}-N-hydroxyformamide LRMS: +ve ion: 459 [M+23], 460 [M+1]. HPLC Rt 1.43 min (214 nm).

EXAMPLE 33

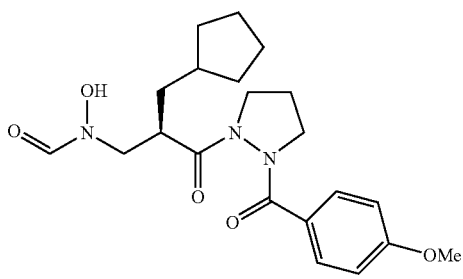

N-{(2R)-Cyclopentylmethyl-3-[2-(4-methoxybenzoyl)-pyrazolidin-1-yl]-3-oxo-propyl}-N-hydroxyformamide LRMS: +ve ion: 426 [M+23], 207. HPLC Rt=4.88 min (214 nm).

EXAMPLE 34

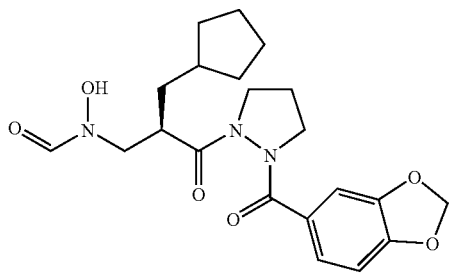

N-{(2R)-Cyclopentylmethyl-3-[2-(benzo[1,3]-dioxole-5-Carbonyl)-pyrazolidin-1-yl]-3-oxo-propyl}N-hydroxyformamide LRMS: +ve ion: 440 [M+23], 221. HPLC Rt=4.75 min (214 nm).

EXAMPLE 35

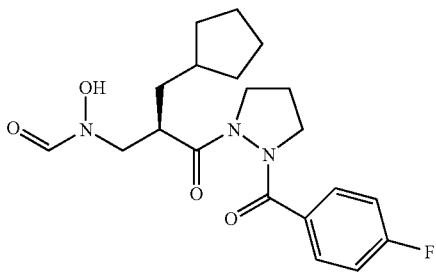

N-{(2R)-Cyclopentylmethyl-3-[2-(4-fluorobenzoyl)-pyrazolidin-1-yl]-3-oxo-propyl}-N-hydroxyformamide LRMS: +ve ion: 414 [M+23], 195. HPLC Rt=4.90 min (214 nm).

EXAMPLE 36

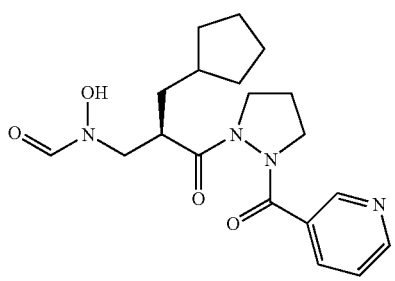

N-{(2R)-Cyclopentylmethyl-3-[2-(pyridine-3-Carbonyl)-pyrazolidin-1-yl]-3-oxo-propyl}N-hydroxyformamide LRMS: +ve ion: 397 [M+23], 178. HPLC Rt=0.99 min (214 nm).

EXAMPLE 37

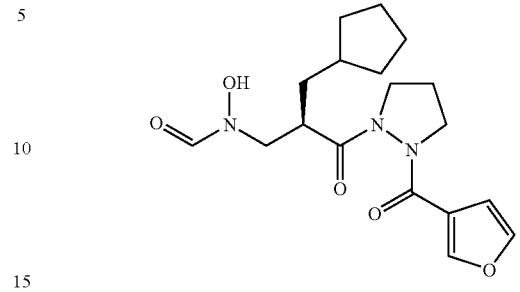

N-{(2R)-Cyclopentylmethyl-3-[2-(furan-3-Carbonyl)-pyrazolidin-1-yl]-3-oxo-propyl}-N-hydroxyformamide LRMS: +ve ion: 386 [M+23], 167. HPLC Rt=4.47 min (214 nm).

EXAMPLE 38

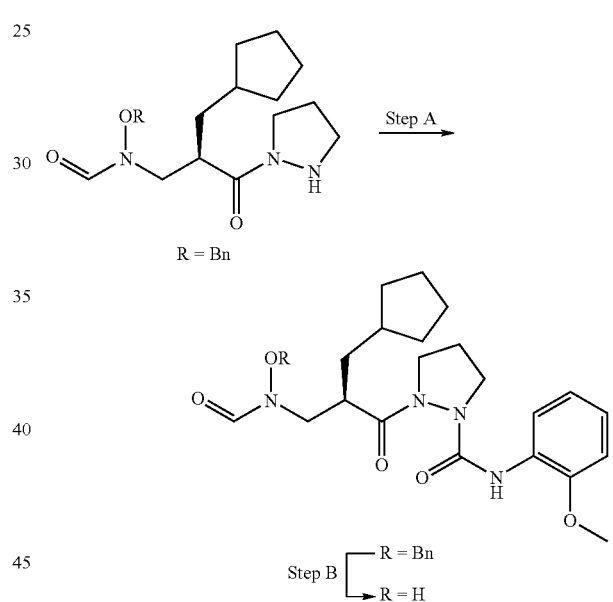

Step A. 2-Methoxyphenyl isocyanate, EtOAc, rt, 16 h; Step B. H$_2$ (g), 10% Pd/C, MeOH, rt, 2 h.

Step A:

2-[3-(Benzyloxyformylamino)-(2R)-cyclopentylmethyl-propionyl]-pyrazolidine-1-Carboxylic acid (2-methoxyphenyl)amide To a solution of N-benzyloxy-N-[(2R)-cyclopentylmethyl-3-oxo-3-pyrazolidin-1-yl-propyl]formamide (37 mg, 0.10 mmol) in EtOAc (2 ml) at rt under argon was added 2-methoxyphenyl isocyanate (15 mg, 0.10 mmol). The resulting mixture was stirred for 16 h at rt and then concentrated under reduced pressure. The crude product was purified by preparative HPLC to give the title compound as a colourless oil (28 mg, 53%). 1H-NMR; δ(CD$_3$OD), 8.29 (0.5H, s, CHO), 8.04–7.90 (1.5H, CHO and ArH), 7.50–7.20 (5H, m, ArH), 7.23–6.87 (3H, ArH), 4.90–4.60 (2H, br m, CH$_2$Ph), 4.25–3.95 (7H, m), 3.83 (3H, s, CH$_3$O), 2.18–1.95 (2H, m), 1.90–0.85 (11H, m). LRMS: +ve ion: 531 [M+23], 360.

Step B:

2-[(2R)-Cyclopentylmethyl-3-(formylhydroxyamino)-propionyl]-pyrazolidine-1-Carboxylic acid (2-methoxyphenyl)amide To a solution of the 2-[3-(benzyloxyformylamino)-(2R)-cyclopentylmethyl-propionyl]-pyrazolidine-1-Carboxylic acid (2-methoxyphenyl)amide (28 mg, 0.055 mmol) in MeOH (2 ml) at rt under argon was added 10% Pd/C (3 mg). Hydrogen gas was bubbled through the black suspension for 15 min and then the reaction was left under an atmosphere of hydrogen for 1 h. After this time, the suspension was filtered and the collected solids were washed with additional MeOH. The combined filtrate and washings were concentrated under reduced pressure to give the title compound as a colourless solid (18 mg, 78%). 1H-NMR; δ(CD₃OD), 8.20–7.65 (2H, br m, CHO and ArH), 7.23–6.87 (3H, m, ArH), 4.30–3.10 (7H, m), 3.85 (1.5H, s, CH₃O), 3.84 (1.5H, s, CH₃O), 2.15–2.00 (2H, m), 1.90–0.90 (11H, m). LRMS: +ve ion: 441 [M+23]. HPLC Rt=5.12 min (214 nm).

The compounds of Example 39–42 were prepared by methods analogous to that of Example 38

EXAMPLE 39

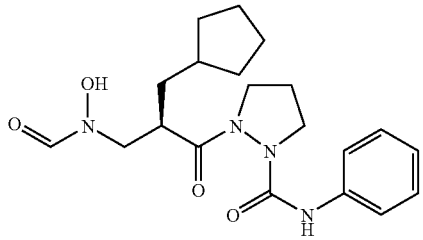

2-[(2R)-Cyclopentylmethyl-3-(formylhydroxyamino)-propionyl]-pyrazolidine-1-Carboxylic acid phenylamide LRMS: +ve ion: 411 [M+23]. HPLC Rt=4.98 min (214 nm).

EXAMPLE 40

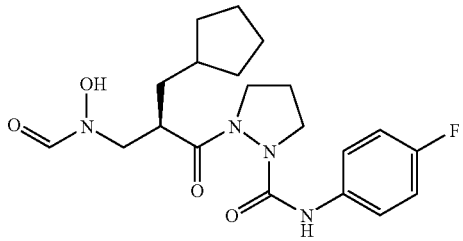

2-[(2R-Cyclopentylmethyl-3-(formylhydroxyamino)-propionyl]-pyrazolidine-1-Carboxylic acid (4-fluorophenyl)amide LRMS: +ve ion: 429 [M+23]. HPLC Rt=5.14 min (214 nm).

EXAMPLE 41

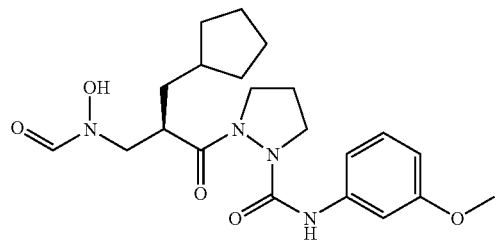

2-[(2R)-Cyclopentylmethyl-3-(formylhydroxyamino)-propionyl]-pyrazolidine-1-Carboxylic acid (3-methoxyphenyl)amide LRMS: +ve ion: 441 [M+23]. HPLC Rt=5.04 min (214 nm).

EXAMPLE 42

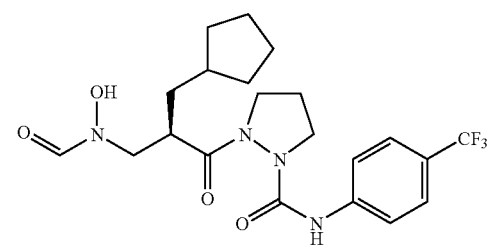

2-[(2R)-Cyclopentylmethyl-3-(formylhydroxyamino)-propionyl]-pyrazolidine-1-Carboxylic acid (4-trifluoromethylphenyl)amide LRMS: +ve ion: 479 [M+23]. HPLC Rt=5.68 min (214 nm).

EXAMPLE 43

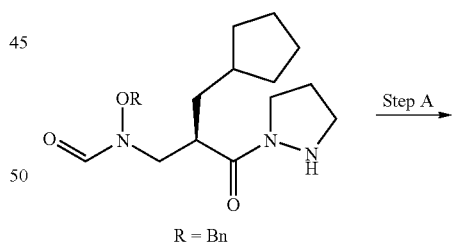

R = Bn

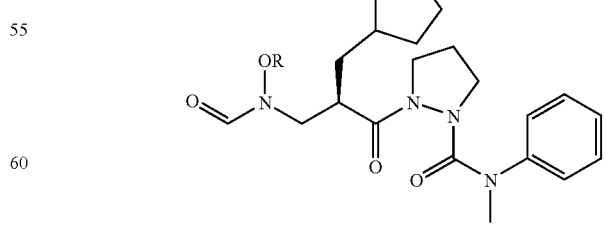

Step B ⎡ R = Bn
       ⎣ R = H

Step A. N-Methyl-N-phenyl carbamoyl chloride, MeCN, DIEA, reflux, 5 h; Step B. H$_2$ (g), 10% Pd/C, MeOH, rt, 2 h.

Step A:

2-[3-(Benzyloxyformylamino)-(2R)-cyclopentylmethyl-propionyl]-pyrazolidine-1-Carboxylic acid methylphenylamide To a solution of N-benzyloxy-N-[(2R)-cyclopentylmethyl-3-oxo-3-pyrazolidin-1-yl-propyl]formamide (72 mg, 0.20 mmol) in MeCN (3 ml) containing DIEA (42 µl, 0.24 mmol) was added N-methyl-N-phenyl carbamoyl chloride (34 mg, 0.20 mmol). The reaction mixture was then heated to reflux where it was maintained for 5 h. After this time the mixture was concentrated under reduced pressure and purified by preparative HPLC. The title compound was isolated as a colourless solid (40 mg, 41%). LRMS: +ve ion: 515 [M+23], 386, 235.

Step B:

2-[(2R)-Cyclopentylmethyl-3-(formylhydroxyamino)-propionyl]-pyrazolidine-1-Carboxylic acid methylphenylamide To a solution of 2-[3-(benzyloxyformylamino)-(2R)-cyclopentylmethyl-propionyl]-pyrazolidine-1-Carboxylic acid methylphenylamide (40 mg, 0.08 mmol) in MeOH (4 ml) at rt under argon was added 10% Pd/C (4 mg). Hydrogen gas was bubbled through the black suspension for 15 min and then the reaction was left under an atmosphere of hydrogen for 2 h. After this time, the suspension was filtered and the collected solids were washed with additional MeOH. The combined filtrate and washings were concentrated under reduced pressure to give the title compound as a colourless solid (31 mg, 95%). 1H-NMR; δ(CD$_3$OD), 8.31 (0.25H, s, CHO), 8.15 (0.25H, s, CHO), 7.97 (0.25H, s, CHO), 7.80 (0.25H, s, CHO), 7.50–7.28 (5H, m, ArH), 4.00–2.60 (7H, m), 3.37 (0.75H, s, NMe), 3.34 (0.75H, s, NMe), 3.31 (1.5H, s, NMe), 2.05–1.35 (11H, m), 1.25–0.95 (2H, m). LRMS: +ve ion: 425 [M+23], 296, 235, 206. HPLC Rt=4.98 min (214 nm).

EXAMPLE 44

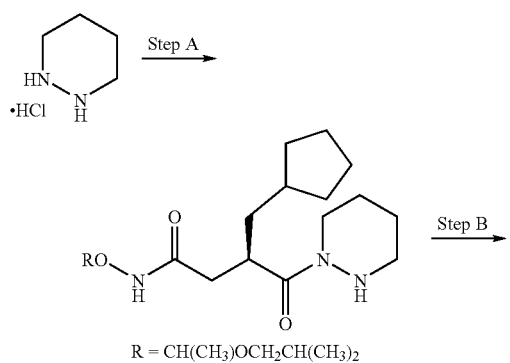

R = CH(CH$_3$)OCH$_2$CH(CH$_3$)$_2$

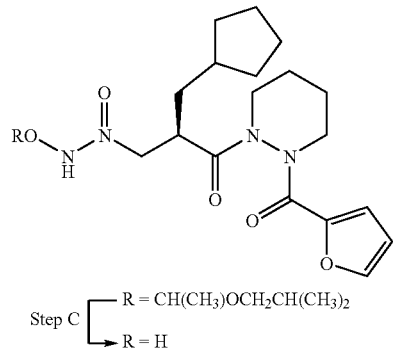

Step C
- R = CH(CH$_3$)OCH$_2$CH(CH$_3$)$_2$
- R = H

Step A. (2R)-Cyclopentylmethyl-N-(1-isobutoxyethoxy)-succinamic acid, EDAC, HOAt, DMF, 0° C. to rt, 16 h; Step B. 2-furoyl chloride, DIEA, CH$_2$Cl$_2$, rt, 1 h; Step C. HCl, MeOH, rt, 2 h.

Step A:

(3R)-Cyclopentylmethyl-N-(1-isobutoxyethoxy)-4-oxo-(tetrahydropyridazin-1-yl)-butyramide To a solution of (2R)-cyclopentylmethyl-N-(1-isobutoxyethoxy)-succinamic acid (482 mg, 1.53 mmol) in CH$_2$Cl$_2$ (5 ml) at 0° C. under argon was added EDAC (323 mg, 1.68 mmol), HOAt (42 mg, 0.306 mmol), 1,2-diazacyclohexane hydrochloride (187 mg, 1.53 mmol), followed by DIEA (586 µl, 3.37 mmol). The resulting solution was stirred at 0° C. for 1 h and then warmed slowly to rt where it was maintained for 18 h. After this time the mixture was concentrated under reduced pressure and the crude residue was partitioned between EtOAc and sat. NaHCO$_3$. The aqueous phase was removed and extracted with additional EtOAc (×2). The combined organic fractions were dried (MgSO$_4$), filtered and concentrated under reduced pressure to give a pale yellow oil. This oil was purified by chromatography on silica eluting with 100% EtOAc to provide the title compound as a colourless oil (136 mg, 23%). LRMS: +ve ion: 406 [M+23], 384 [M+1]. 1H-NMR; δ(CDCl$_3$), 8.53 (0.5H, br s, NH), 8.40 (0.5H, br s, NH), 4.95–4.87 (1H, m, OCHO), 4.02–3.15 (6H, m), 3.10–2.80 (2H, m), 2.55–2.20 (1H, m), 1.90–1.30 (15H, m), 1.36 (1.5H, d, J=5 Hz, CH$_3$CH), 1.35 (1.5H, d, J=5 Hz, CH$_3$CH), 1.20–1.00 (2H, m), 0.92 (6H, d, J=6.5 Hz).

Step B:

(3R)-Cyclopentylmethyl4-[2-(furan-2-Carbonyl)-tetrahydropyridazin-1-yl]-N-(1-isobutoxyethoxy)-4-oxo-butyramide To a solution of (3R)-cyclopentylmethyl-N-(1-isobutoxyethoxy)-4-oxo-(tetrahydropyridazin-1-yl)-butyramide (65 mg, 0.17 mmol) in CH$_2$Cl$_2$ (2 ml) containing DIEA (32 µl, 0.19 mmol) at rt under argon was added 2-furoyl chloride (22 mg, 0.17 mmol). The reaction mixture was stirred for 1 h at rt and then washed with 1M citric acid,1M Na$_2$CO$_3$ and sat. NaCl. The organic layer was dried (MgSO$_4$), filtered and concentrated under reduced pressure to give a colourless foam. The crude product was used without further purification (74 mg, 91%). LRMS: +ve ion: 500 [M+23], 478 [M+1], 404.

Step C:

(3R)-Cyclopentylmethyl-4-[2-(furan-2-Carbonyl)-tetrahydropyridazin-1-yl]-N-hydroxy-4-oxo-butyramide To a solution of (3R)-cyclopentylmethyl-4-[2-(furan-2-Carbonyl)-tetrahydropyridazin-1-yl]-N-(1-isobutoxyethoxy)-4-oxo-butyramide (74 mg, 0.16 mmol) in MeOH (2 ml) at rt in air was added aq. HCl (171 µl of a 1M solution, 0.17 mmol). The resulting solution was stirred for 2 h at rt. After this time the reaction was concentrated under reduced pressure and the crude product was purified by preparative HPLC to give the title compound as a colourless solid (32 mg, 55%). 1H-NMR; δ(CH₃OD), 7.80–7.60 (1H, m, HetArH), 7.20–7.05 (1H, br m, HetArH), 6.67–6.50 (1H, br m, HetArH), 4.70–4.30 (2H, br m), 3.60–3.40 (1H, br m), 3.40–2.80 (2H, br m), 2.52–2.28 (2H, m), 1.90–0.70 (15H, br m). LRMS: +ve ion: 400 [M+23], 378 [M+1], 345, 181. HPLC Rt=4.75 min (214 nm).

EXAMPLE 45

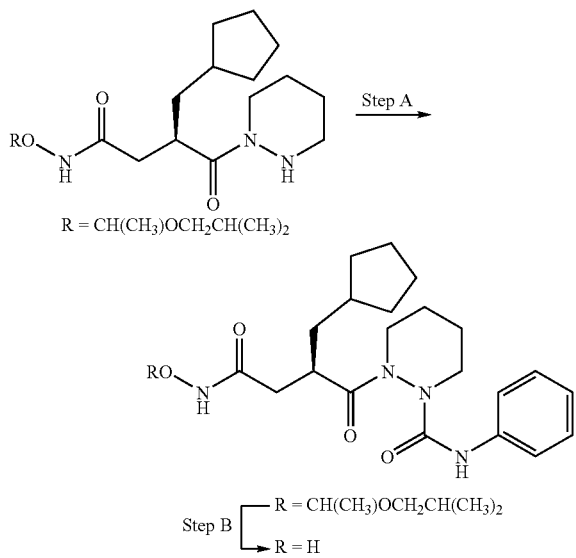

R = CH(CH₃)OCH₂CH(CH₃)₂

Step B [ R = CH(CH₃)OCH₂CH(CH₃)₂
         R = H

Step A. 3,5-Bis-(trifluoromethyl)phenyl isocyanate, EtOAc, rt, 16 h; Step B. HCl, MeOH, rt, 4 h.

Step A:

2-[(2R)-Cyclopentylmethyl-3-(1-isobutoxyethoxycarbamoyl)-propionyl]-tetrahydropyridazine-1-Carboxylic acid phenylamide To a solution of (3R)-cyclopentylmethyl-N-(1-isobutoxyethoxy)-4-oxo-(tetrahydropyridazin-1-yl)-butyramide (65 mg, 0.17 mmol) in EtOAc (2 ml) at rt under argon was added phenyl isocyanate (20 mg, 0.17 mmol). The resulting mixture was stirred for 16 h at rt and then concentrated under reduced pressure to give a colourless foam. The crude product was used without further purification (assumed quantitative yield, 0.17 mmol). LRMS: +ve ion: 525 [M+23], 503 [M+1], 370, 310, 251.

Step B:

2-[(2R)-Cyclopentylmethyl-3-hydroxycarbamoylpropionyl]-tetrahydropyridazine-1-Carboxylic acid phenylamide To a solution of 2-[(2R)-cyclopentylmethyl-3-(1-isobutoxyethoxycarbamoyl)-propionyl]-tetrahydropyridazine-1-Carboxylic acid phenylamide (0.17 mmol) in MeOH (2 ml) at rt in air was added aq. HCl (187 µl of a 1M solution, 0.19 mmol). The resulting solution was stirred for 4 h at rt. After this time the reaction was concentrated under reduced pressure and the crude product was purified by preparative HPLC to give the title compound as a colourless solid (30 mg, 44%). 1H-NMR; δ(CH₃OD), 7.67–7.57 (1H, m, ArH), 7.47–7.44 (1H, m, ArH), 7.32–7.24 (2H, m, ArH), 7.11–6.99 (1H, m, ArH), 4.60–4.30 (2H, br m), 4.90–2.30 (5H, m), 1.90–0.90 (15H, m). LRMS: +ve ion 400 [M+23], 378 [M+1], 345, 181. HPLC Rt=5.15–5.46 min [rotamers] (214 nm).

BIOLOGICAL EXAMPLE

Minimal Inhibitory concentrations (MIC) of inhibitors against clinical isolates of S. pneumoniae, H. influenzae and M. catarrhalis obtained from the Public Health and Clinical Microbiology Laboratory, Addenbrooke's Hospital, Hills Road, Cambridge CB2 2QW, UK, were determined by a standard agar plate dilution method following recommended in British Society for Antimicrobial Chemotherapy Working Party. 1991. "A guide to sensitivity testing British Society for Antimicrobial Chemotherapy, London, United Kingdom". Briefly Iso-Sensitest agar (pH 7.2: Oxoid, United Kingdom) was employed supplemented with 5% horse blood (Oxoid) and 20 µg of NAD (Sigma) per ml to support growth of fastidious bacteria. The inoculum used was approximately $10^4$ colony forming units of each isolate contained in a volume of 1 µl. Plates were incubated 18 to 24 hr in air, or for fastidious bacteria an atmosphere enriched with 4–6% carbon dioxide at 35° C. The MIC was determined as the lowest concentration of an antimicrobial tested that inhibited growth of the inoculum, disregarding a single persisting colony or faint haze caused by the inoculation.

The compounds of the Examples were are antibacterially active in the above assays, The following table states the MICs or MIC ranges of the tested compounds against 6 strains of S. pneumoniae, 4 strains of H. influenzae and 3 strains of M. catarrhalis.

| Example | S. pneumoniae µg/ml | H. Influenzae µg/ml | M. catarrhalis µg/ml |
|---|---|---|---|
| 1 | 0.5–2 | <0.125–0.25 | <0.125 |
| 2 | 1–8 | 0.25–8 | 0.25 |
| 3 | 0.5–2 | 1–4 | 0.125 |
| 4 | 0.5–4 | 16->32 | 0.5 |
| 5 | 2–16 | 208 | 0.25 |
| 6 | 0.5–2 | 4–8 | 0.06 |
| 7 | 0.5–4 | 1->32 | 0.5 |
| 8 | 0.5–4 | 1–8 | 0.5 |
| 9 | 0.5–2 | 0.125–8 | <0.93 |
| 10 | 0.5–4 | 0.5–2 | 0.5 |
| 11 | 0.5–4 | 0.25–2 | 0.25 |
| 12 | 2–16 | 16–32 | 1 |
| 13 | 8–16 | 8->16 | 2 |
| 14 | 2–4 | <0.125–4 | <0.125 |
| 15 | 2–4 | <0.125–4 | <0.125 |
| 16 | 4–8 | <0.125–4 | <0.125 |
| 17 | 4–8 | 0.125 | <0.125 |
| 18 | 4 | 0.25–16 | <0.125 |
| 19 | 2–4 | <0.125–4 | <0.125 |
| 20 | 4–8 | 0.5–2 | <0.03 |
| 21 | 1–4 | 4–16 | 0.125 |
| 22 | 4–16 | 8->16 | 2 |
| 23 | 8–16 | 0.5–2 | <0.125 |
| 24 | 4–16 | 1–4 | <0.125 |
| 25 | 4–8 | <0.125–1 | <0.125 |
| 26 | 8 | 1–8 | 0.125 |
| 27 | 16 | 2–16 | 0.06 |

-continued

| Example | S. pneumoniae µg/ml | H. Influenzae µg/ml | M. catarrhalis µg/ml |
|---|---|---|---|
| 28 | 0.5–4 | 16 | 0.06 |
| 29 | 4–8 | 2–16 | 0.06 |
| 30 | 16–32 | 2->32 | 0.125 |
| 31 | 8 | 4–16 | 0.06 |
| 32 | 1–8 | 16 | 0.25 |
| 33 | 4–16 | 16–32 | 0.06 |
| 34 | 8–16 | 4–16 | 0.125 |
| 35 | 16 | 4–8 | 0.125 |
| 36 | 8 | 2–32 | 0.125 |
| 37 | 4 | 1->32 | 0.06 |
| 38 | 8–16 | 1–2 | 0.25 |
| 39 | 4–16 | <0.125–2 | <0.125 |
| 40 | 8–16 | <0.125–2 | <0.125 |
| 41 | 4–8 | <0.125–2 | <0.125 |
| 42 | 2–8 | 2–8 | Not tested |
| 43 | 8->32 | 16–32 | 8 |
| 44 | 2–4 | 0.06–0.125 | 0.6 |
| 45 | 4–8 | 1–4 | Not Tested |

The invention claimed is:

1. A compound of formula (I) or a pharmaceutical or veterinary acceptable salt, hydrate or solvate thereof

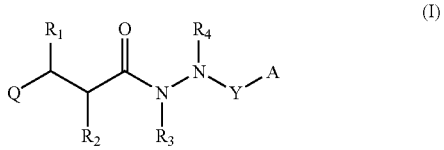

wherein Q represents a radical of formula —N(OH)CH(=O) or formula —C(=O)NH(OH);

Y represents —C(=O)—, —C(=S)—, —S(=O)—, or —SO$_2$—;

$R_1$ represents hydrogen, $C_1$–$C_6$ alkyl or $C_1$–$C_6$ alkyl substituted by one or more halogen atoms, or, except when Q is a radical of formula —N(OH)CH(=O), a hydroxy, $C_1$–$C_6$ alkoxy, $C_1$–$C_6$ alkenyloxy, halogen, amino, $C_1$–$C_6$ alkylamino, or di-($C_1$–$C_6$ alkyl)amino group;

$R_2$ represents a substituted or unsubstituted $C_1$–$C_6$ alkyl, $C_1$–$C_3$ alkyl-O—$C_1$–$C_3$ alkyl, $C_1$–$C_3$ alkyl-S—$C_1$–$C_3$ alkyl, cycloalkyl($C_1$–$C_3$ alkyl)-, aryl($C_1$–$C_3$ alkyl)-, heterocyclyl($C_1$–$C_3$ alkyl)-, or $R^1R^2N$—$C_1$–$C_3$ alkyl group wherein $R^1$ represents hydrogen or $C_1$–$C_3$ alkyl and $R^2$ represents $C_1$–$C_3$ alkyl, or $R^1R^2N$-represents a cyclic amino group;

$R_3$ and $R_4$ taken together with the nitrogen atoms to which they are respectively attached form a saturated heterocyclic ring of from 4 to 7 ring atoms, which may be fused to a second carbocyclic or heterocyclic ring, either of which rings may optionally be substituted; and A represents a primary, secondary or tertiary amino group or a group —$R_5$, —$OR_5$, wherein $R_5$ is a substituted or unsubstituted $C_1$–$C_6$ alkyl, $C_2$–$C_6$ alkenyl, $C_2$–$C_6$ alkynyl, cycloalkyl, aryl, heterocyclyl, $C_1$–$C_3$ alkyl-O—$C_1$–$C_3$ alkyl, $C_1$–$C_3$ alkyl-S—$C_1$–$C_3$ alkyl, cycloalkyl($C_1$–$C_3$ alkyl)-, heterocyclic($C_1$–$C_3$ alkyl, aryl($C_1$–$C_3$ alkyl)-, or $R^1R^2N$—$C_1$–$C_3$ alkyl group wherein $R^1$ represents hydrogen or $C_1$–$C_3$ alkyl and $R^2$ represents $C_1$–$C_3$ alkyl, or $R^1R^2N$-represents a cyclic amino group.

2. A compound as claimed in claim 1 wherein Q is an N-formyl hydroxylamine group —N(OH)CH(=O).

3. A compound as claimed in claim 1 wherein —Y— is —C(=O)— or $SO_2$.

4. A compound as claimed in claim 1 wherein $R^1$ is hydrogen.

5. A compound as claimed in claim 1 wherein $R^2$ is optionally substituted $C_1$–$C_6$ alkyl, $C_3$–$C_6$ alkenyl, $C_3$–$C_6$ alkynyl or cycloalkyl;

phenyl($C_1$–$C_6$ alkyl)-, phenyl($C_3$–$C_6$ alkenyl)- or phenyl ($C_3$–$C_6$ alkynyl)- optionally substituted in the phenyl ring;

cycloalkyl($C_1$–$C_6$ alkyl)-, cycloalkyl ($C_3$–$C_6$ alkenyl)- or cycloalkyl($C_3$–$C_6$ alkynyl)-optionally substituted in the cycloalkyl ring; or $CH_3(CH_2)_pO(CH_2)_q$- or $CH_3(CH_2)_pS(CH_2)_q$-, wherein p is 0,1, 2 or 3 and q is 1, 2 or 3.

6. A compound as claimed in claim 1 wherein $R_2$ is methyl, ethyl, n- or iso-propyl, n-or iso-butyl, n-pentyl, iso-pentyl, 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-Chlorophenyl)prop-2-yn-1-yl, but-2-yn-1-yl, cyclopentyl, cyclohexyl, cyclopentylmethyl, cyclopentylethyl, cyclopentylpropyl, acyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, pyrid-2-ylmethyl, pyrid-3-ylmethyl, pyrid-4-ylmethyl, phenylpropyl, 4-Chlorophenylpropyl, 4-methylphenylpropyl, 4-methoxyphenylpropyl, benzyl, 4-Chlorobenzyl, 4-methylbenzyl, or 4-methoxybenzyl.

7. A compound as claimed in claim 1 wherein $R_2$ is ($C_1$–$C_6$)alkyl-, cycloalkylmethyl-, ($C_1$–$C_3$)alkyl-S—($C_1$–$C_3$)alkyl-, or ($C_1$–$C_3$)alkyl-O—($C_1$–$C_3$)alkyl-, especially n-propyl, n-butyl, n-pentyl, cyclopentylmethyl, cyclopentylethyl, cyclohexylmethyl or cyclohexylethyl.

8. A compound as claimed in claim 1 wherein the ring formed by $R_3$ and R4 and the nitrogens to which they are attached is one of the following, any of which may be optionally substituted, and wherein r represents hydrogen or $C_1$–$C_4$ alkyl and any sulfur atom present as a ring member may be oxidized to —SO— or —$SO_2$—:

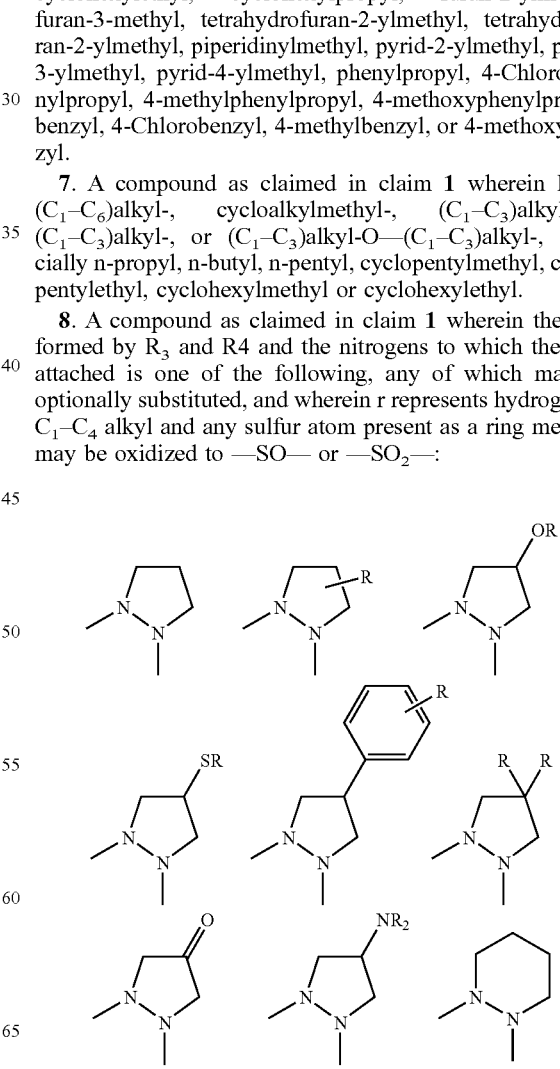

-continued

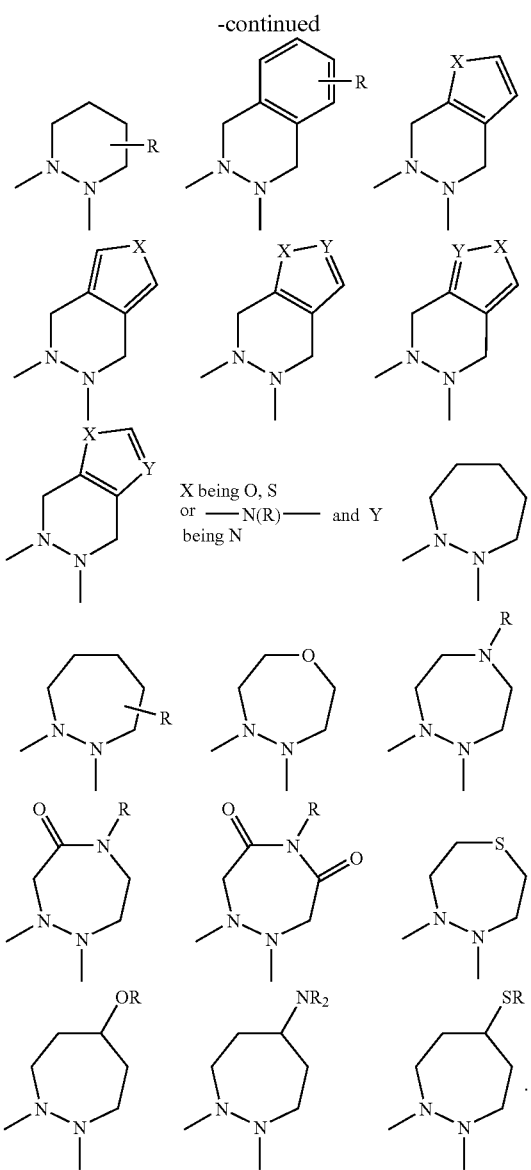

9. A compound as claimed in claim 1 wherein A is a secondary amino group or a cyclic or non-cyclic tertiary amino group.

10. A compound as claimed in claim 1 wherein A is an amino group of formula —NR$_6$R$_7$ wherein R$_6$ and R$_7$ independently represent a radical of formula (II)

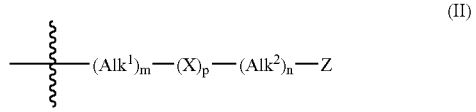

wherein
m, p and n are independently 0 or 1;
Z represents hydrogen or a carbocyclic or heterocyclic ring of 5 to 7 ring atoms which is optionally fused to a saturated or unsaturated carbocyclic or heterocyclic second ring of 5 to 7 ring atoms;

Alk$^1$ and Alk$^2$ independently represent divalent C$_1$–C$_3$ alkylen radicals;
X represents —O—, —S—, —S(O)—, —S(O$_2$)—, —C(=O)—, —NH—, —NR$_7$— where R$_7$ is C$_1$–C$_3$ alkyl;
and wherein
Alk$^1$ and Alk$^2$ and Z when other than hydrogen, independently are optionally substituted by
(C$_1$–C$_3$)alkyl, (C$_2$–C$_3$)alkenyl, or (C$_2$–C$_3$)alkynyl,
phenyl, optionally substituted by (C$_1$–C$_3$)alkyl, (C$_1$–C$_3$) alkoxy, halo, nitro, amino, mono- or di-(C$_1$–C$_3$3) alkylamino, cyano or trifluoromethyl;
monocyclic 5 or 6-membered heterocyclic, optionally substituted by (C$_1$–C$_3$)alkyl, (C$_1$–C$_3$ alkoxy, halo, nitro, amino, mono- or di- (C$_1$–C$_3$)alkylamino, cyano or trifluoromethyl
benzyl, optionally substituted in the phenyl ring by (C$_1$–C$_3$)alkyl, (C$_1$–C$_3$)alkoxy, halo, nitro, amino, mono- or di-(C$_1$–C$_3$)alkylamino, cyano or trifluoromethyl,
hydroxy, phenoxy, (C$_1$–C$_6$)alkoxy, or hydroxyl (C$_1$–C$_6$)alkyl,
mercapto,(C$_1$–C$_6$) alkylthio or mercapto (C$_1$–C$_6$)alkyl,
oxo,
nitro,
cyano
halo
—COOH, or —COOR$^A$,
—COONH$_2$, —CONHR$^A$, or —CONR$^A$R$^B$
—COR$^A$, —SO$_2$R$^A$,
—NHCOR$^A$,
—NH$_2$, —NHR$^A$, or —NR$^A$R$^B$,
wherein R$^A$ and R$^B$ are independently a (C$_1$–C$_6$) alkyl group, R$^A$ and R$^B$ taken together with the nitrogen atom to which they are attached form a 5- or 6-membered heterocyclic ring which may be sutstituted by (C$_1$–C$_3$)alkyl, hydroxyl, or hydroxyl(C$_1$–C$_6$)alkyl.

11. A compound as claimed in claim 10 wherein Alk$^1$ and Alk$^2$ independently represent —(CH$_2$)— or —(CH$_2$CH$_2$)—.

12. A compound as claimed in claim 10 wherein m is 0, p is 1, n is 0 or 1 and X is —C(=O)— or —S(O$_2$)—.

13. A compound as claimed in claim 10 wherein the substituent (II) has the formula —CH$_2$Z, —OZ, or —(C=O)Z wherein Z is C$_1$–C$_3$ alkyl, phenyl, 3,4-methlenedioxyphenyl, morpholinyl, pyrimidinyl, 1,2,3-thiadiazolyl, 1,4-thiazolyl, benzofuranyl, furanyl, thienyl, pyranyl, pyrrolyl, pyrazolyl, isoxazolyl, or pyridyl, any of which may optionally be substituted as specified. In particular, Z may be a methyl, ethyl, n- or iso-propyl, phenyl, 3,4-methylenedioxyphenyl, morpholinyl, pyrimidin-2-yl, 1,2,3-thiadiazol-5-yl, 1,4-thiazol-5-yl, benzofuran-2-yl, 2- or 3-furanyl, 2- or 3-thienyl, 2- or 3-pyranyl, 2-, 3- or 4-pyrrolyl, 3-, 4- or 5-pyrazolyl, 3-, 4- or 5-isoxazolyl, or 2-, 3- or 4-pyridyl ring any of which may optionally be substituted.

14. A compound as claimed in claim 1 wherein A is an amino group of formula —NR$_6$R$_7$ wherein R$_6$ and R$_7$ taken together with the nitrogen atom to which they are attached form a saturated heterocyclic ring of 5 to 8 atoms optionally fused to a saturated or unsaturated carbocyclic or heterocyclic second ring of 5 to 7 ring atoms, any of which rings being optionally substituted by a radical of formula (II)

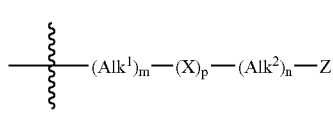

(II)

wherein
m, p and n are independently 0 or 1;
Z represents hydrogen or a carbocyclic or heterocyclic ring of 5 to 7 ring atoms which is optionally fused to a saturated or unsaturated carbocyclic or heterocyclic second ring of 5 to 7 ring atoms;
$Alk^1$ and $Alk^2$ independently represent divalent $C_1$–$C_3$ alkylen radicals;
X represents —O—, —S—, —S(O)—, —S($O_2$)—, —C(=O)—, —NH—, —$NR_7$— where $R_7$ is $C_1$–$C_3$ alkyl;
and wherein
$Alk^1$ and $Alk^2$ and Z when other than hydrogen, independently are optionally substituted by
($C_1$–$C_3$)alkyl, ($C_2$–$C_3$)alkenyl, or ($C_2$–$C_3$)alkynyl,
phenyl, optionally substituted by ($C_1$–$C_3$)alkyl, ($C_1$–$C_3$) alkoxy, halo, nitro, amino, mono- or di-($C_1$–$C_3$3) alkylamino, cyano or trifluoromethyl;
monocyclic 5 or 6-membered heterocyclic, optionally substituted by ($C_1$–$C_3$)alkyl, ($C_1$–$C_3$ alkoxy, halo, nitro, amino, mono- or di- ($C_1$–$C_3$)alkylamino, cyano or trifluoromethyl
benzyl, optionally substituted in the phenyl ring by ($C_1$–$C_3$)alkyl, ($C_1$–$C_3$)alkoxy, halo, nitro, amino, mono- or di-($C_1$–$C_3$)alkylamino, cyano or trifluoromethyl,
hydroxy, phenoxy, ($C_1$–$C_6$)alkoxy, or hydroxyl ($C_1$–$C_6$)alkyl,
mercapto, ($C_1$–$C_6$) alkylthio or mercapto ($C_1$–$C_6$)alkyl,
oxo,
nitro,
cyano
halo
—COOH, or —$COOR^A$,
—$COONH_2$, —$CONHR^A$, or —$CONR^AR^B$
—$COR^A$, —$SO_2R^A$,
—$NHCOR^A$,
—$NH_2$, —$NHR^A$, or —$NR^AR^B$,
wherein $R^A$ and $R^B$ are independently a ($C_1$–$C_6$) alkyl group, $R^A$ and $R^B$ taken together with the nitrogen atom to which they are attached form a 5- or 6-membered heterocyclic ring which may be sustituted by ($C_1$–$C_3$)alkyl, hydroxyl, or hydroxyl ($C_1$–$C_6$)alkyl.

15. A compound as claimed in claim 14 wherein A is optionally substituted piperidin-1-yl or 1-piperazinyl.

16. A compound as claimed in claim 1 of formula (IIA) or (IIB)

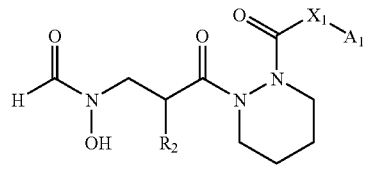

(IIA)

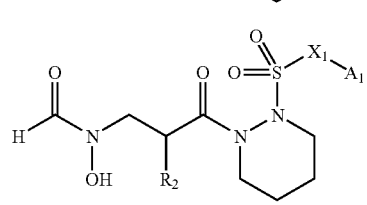

(IIB)

wherein $R_2$ is as defined in claim 1;
$X_1$ is a bond, $C_1$–$C_3$ alkylene, —NH— or —O—;
and $A_1$ is optionally substituted $C_1$–$C_6$ alkyl, cycloalkyl, aryl, or heterocyclic.

17. A compound as claimed in claim 16 wherein $R_2$ is n-propyl, n-butyl, n-pentyl, cyclopentylmethyl, cyclopentylethyl, cyclohexylmethyl or cyclohexylethyl;
$X_1$ is a bond, —$CH_2$—, —$CH_2CH_2$—, —$CH_2CH_2CH_2$—, —NH— or —O—; and
$A_1$ is methyl, ethyl phenyl, cyclopentyl, cyclohexyl, 2- or 3-furanyl, 2- or 3-thienyl, 2-, 3- or 4-pyridyl, 3-, 4- or 5-pyrazolyl, 3-, 4-or 5-oxazolyl, or 3-, 4- or 5-thiazolyl, methoxymethyl, 3,5-bis- (trifluoromethyl) phenyl, 4-trifluoromethylphenyl, 4methoxyphenyl, 3,4-methylenedioxyphenyl, 4-fluorophenyl benzyl, 3-pyridyl, 4-pyridyl, cyclohexyl, 1,3-dimethylpyrazol-5-yl, 1-methylimidazol-5-yl, or 2-[morpholin-1-yl]pyrid-5-yl.

18. A method for the treatment of bacterial infections in humans and non-human mammals, which comprises administering to a subject suffering such infection an antibacterially effective dose of a compound as claimed in claim 1.

19. A method of inhibiting bacterial growth in vitro and in vivo in mammals comprising applying a compound as claimed in claim 1.

20. A method for the treatment of bacterial contamination by applying an antibacterially effective amount of a compound as claimed in claim 1 to the site of contamination.

21. A pharmaceutical or veterinary composition comprising a compound as claimed in claim 1 together with a pharmaceutically or veterinarily acceptable carrier or excipient.

* * * * *